(12) United States Patent
Druzgala et al.

(10) Patent No.: US 7,498,449 B2
(45) Date of Patent: Mar. 3, 2009

(54) ANTIARRHYTHMIC PRECURSOR COMPOUNDS, METHODS OF SYNTHESIS AND METHODS OF USE

(75) Inventors: Pascal Druzgala, Santa Rosa, CA (US); Jien-Heh J. Tien, Pacifica, CA (US); Arthur J. Cooper, Mentor, OH (US); Cyrus Becker, Fremont, CA (US)

(73) Assignee: ARYx Therapeutics, Fremont, CA (US)

( * ) Notice: Subject to any disclaimer, the term of this patent is extended or adjusted under 35 U.S.C. 154(b) by 210 days.

(21) Appl. No.: 11/457,719

(22) Filed: Jul. 14, 2006

(65) Prior Publication Data

US 2007/0060640 A1 Mar. 15, 2007

Related U.S. Application Data

(60) Provisional application No. 60/699,780, filed on Jul. 15, 2005.

(51) Int. Cl.
C07D 493/00 (2006.01)
C07D 307/93 (2006.01)
C07D 307/00 (2006.01)

(52) U.S. Cl. .................. 549/282; 549/462; 549/468

(58) Field of Classification Search .......... 549/282, 549/462, 468
See application file for complete search history.

(56) References Cited

U.S. PATENT DOCUMENTS

| 3,248,401 | A | 4/1966 | Tondeur et al. |
| 4,575,513 | A | 3/1986 | Descamps et al. |
| 4,931,464 | A | 6/1990 | Grover et al. |
| 4,962,095 | A | 10/1990 | Grover et al. |
| 5,175,187 | A | 12/1992 | Baligadoo |
| 5,364,880 | A | 11/1994 | Druzgala |
| 5,440,054 | A | 8/1995 | Druzgala |
| 5,849,788 | A | 12/1998 | Druzgala |
| 6,130,240 | A | 10/2000 | Druzgala |
| 6,316,487 | B1 | 11/2001 | Druzgala et al. |
| 6,362,223 | B1 | 3/2002 | Druzgala et al. |
| 6,372,783 | B1 | 4/2002 | Druzgala et al. |
| 6,683,195 | B2 | 1/2004 | Druzgala et al. |

FOREIGN PATENT DOCUMENTS

| EP | 0425359 A1 | 5/1991 |
| EP | 1 299 247 A | 1/2002 |
| JP | 05025044 A | 2/1993 |
| WO | 90/07330 | 7/1990 |
| WO | 92/20331 | 11/1992 |
| WO | 94/29289 | 12/1994 |
| WO | 01/29018 | 4/2001 |
| WO | 03/050102 | 6/2003 |

OTHER PUBLICATIONS

Fazio et al., Recent Progress in Hormone Research (2004), vol. 59, 31-50.*

Bennett et al., Journal of the Chemical Society, Perkin Transactions 1: Organic and Bio-Organic Chemistry (1972-1999) (1979), (12), 2990-4.*

Juhasz et al.: "Cardiovascular studies on different classes of soft drugs," Pharmazie, VEB Berlag Volk und Gesundheit. Berline, DD, vol. 55, No. 3, 2000, pp. 228-238, XP002164943.

Cairns, John A., Stuart J. Connolly, Robin Roberts et al. (Mar. 8, 1997) "Randomized trial of outcome after myocardial infarction in patients with frequent or repetitive ventricular premature depolarization: CAMIAT" The Lancet, vol. 349, pp. 675-682.

Connolly, S. J. Cairnes, M. Gent et al. (Nov. 15, 1997) "Effect of prophylactic amiodarone on mortality after acute myocardial infarction and in congestive heart failure: meta-analysis of individual data from 6500 patients in randomized trials," The lancet, vol. 350, pp. 1417-1424.

Julian, D.G., A.J. Camm, G. Frangin et al. (Mar. 8, 1997) "Randomised trial of effect of amiodarone on mortality in patients with left-ventricular dysfunction after recent myocardial infarction: EMIAT," The Lancet, vol. 349, pp. 667-674.

Kerr, Charles R., Mauricio B.Rosenbaum, Pablo A. Chiale (1996) "Amiodarone In: Cardiovascular Drug Therapy," Editor: Messerli, F.H.W.B. Saunders Co., 2nd Edition, Chapter 138, pp. 1247-1264.

Kowey, Peter R., Joseph H. Levine, John M. Herre et al. (Dec. 1, 1995) "Randomized, Double-Blind Comparison of Intravenous Amiodarone and Bretylium in the Treatment of Patients with Recurrent, Hemodynamically Destabilizing Ventricular Tachycardia or Fibrillation," Circulation, vol. 92, No. 11, pp. 3255-3263.

(Continued)

Primary Examiner—D. Margaret Seaman
Assistant Examiner—Niloofar Rahmani
(74) Attorney, Agent, or Firm—McDonnell Boehnen Hulbert & Berghoff LLP

(57) ABSTRACT

The invention comprises compounds of Formula 1:

Formula 1 wherein, $R_1$ is independently H or halogen; $R_2$ is, for example, H or $-R_{10}-NR_{11}R_{12}$, and wherein $R_{10}$ is $C_1$-$C_6$ alkyl, and $R_{11}$ and $R_{12}$ are independently H, $C_1$-$C_4$ alkyl, and hydrates, solvates, salts and tautomers thereof. The invention further comprises methods for making the compounds of the invention and methods for making compounds useful in the treatment or prevention of cardiac arrhythmia from the compounds of the invention.

6 Claims, No Drawings

OTHER PUBLICATIONS

Naccarelli, Gerald, Robert L. Rinkenberger, Anne H. Dougherty, Ruth Giebel (Nov./Dec. 1985) "Evaluations of New Drugs, Amiodarone: Pharmacology and Antiarrhythmic and Adverse Effects," Pharmacotherapy 5(6):298-313.

Rosenbaum, Mauricio B., Pablo A. Chiale, M. Susana Halpern et al. (Dec. 1976) "Clinical Efficacy of Amiodarone as an Antiarrhythmic Agent," The American Journal of Cardiology, vol. 38, pp. 934-944.

Rosenbaum, Mauricio, Pablo A. Chiale, David Ryba, Marcelo V. Elizari (Aug. 1974) "Control of Tachyarrhythmias Associated with Wolff-Parkinson-White Syndrome by Amiodarone Hydrochloride," The American Journal of Cardiology, vol. 34, pp. 215-223.

Singh, B.N. and E.M. Vaughan Williams (1970) "The effect of amiodarone, a new anti-anginal drug, on cardiac muscle," Br. J. Pharmacol, vol. 39, pp. 657-667.

Vrobel, Thomas R., Paul E. Miller, Nelson D. Mostow, Louis Rakita (May/Jun. 1989) "A General Overview of Amiodarone Toxicity: Its Prevention, Detection, and Management," Progress in Cardiovascular Diseases, vol. 31, No. 6, pp. 393-426.

Sami, Magdi H. (1991) "Sudden Death in Congestive Heart Failure," Journal Clin. Pharmacol. vol. 31, pp. 1081-1084.

Smith, William McFate (1985): Epidemiology of Congestive Heart Failure, The American Journal of Cardiology 55:3A-8A.

Glodstein, Sidney (1991) "Identification of Patients at Risk for Sudden Death in Congestive Heart Failure," Journal of Clinical Pharmacol, vol. 31, pp. 1085-1088.

The Cardiac Arrhythmia Suppression Trial (CAST) Investigators (1989) "Preliminary Report: Effect of Encainide and Flecainide on Mortality in a Randomized Trial of Arrhythmia Suppression after Myocardial Infarction," The New England Journal of Medicine, vol. 321, o.6, pp. 46-412.

Bigger, J. Thomas (1987) Why patients with congestive heart failure die: arrhythmias and sudden cardiac death, Circulation 75 (suppl IV):28-35.

Abdollah, Hoshiar et al.:"Antiarrhythmic Effects of Desethylamiodarone in Dogs with Subacute Myocardial Infarction and Inducible Ventricular Arrythmias," Journal of Cardiovascular Pharmacology, 13(1), 37-44 Coden: JCPCDT; ISSN: 0160-2446, 1989, XP008050098.

R. Charlier et al.: "Recherches dans la serie des benzofuranes," Cardiologia, vol. 54, pp. 83-90 (1969).

Xu, Yuhgen et al. (1992) "Synthesis of 3-substituted dilodobenzoylidole derivatives" Chemical Abstracts, vol. 116, No. 5, pp. 756.

Database CA [Online], Chemical Abstracts Service, Columbus, Ohio, US; Mukhanova, T.I., et al., "Acetals of lactams and amides of acids. Part 76. New approach to the synthesis of benzofuro[3,2-c]pyridine derivatives", XP002411508, retrieved from STN Database accession No. 1996:393853 abstract & Khimiko-Farmatsevticheskii Zhurnal, 30(3), 54-56 Coden: KHFZAN; ISSN: 0023-1134, 1996.

* cited by examiner

ANTIARRHYTHMIC PRECURSOR COMPOUNDS, METHODS OF SYNTHESIS AND METHODS OF USE

BACKGROUND OF THE INVENTION

Congestive heart failure (CHF) is a disease affecting approximately 2% of the population of the United States (Sami, M. H. [1991] J. Clin. Pharmacol. 31:1081). Despite advances in the diagnosis and treatment of CHF, the prognosis remains poor with a 5-year mortality rate higher than 50% from the time of diagnosis (McFate Smith, W. [1985] Am. J. Cardiol. 55:3A; McKee, P. A., W. P. Castelli, P. M. McNamara, W. B. Kannel [1971] N. Engl. J. Med. 285:1441). In patients with CHF, the rate of survival is lowest in those patients with severe depression of left ventricular function and patients who have frequent ventricular arrhythmias. Patients with ventricular arrhythmias and ischemic cardiomyopathy have an increased risk of sudden death. The presence of ventricular tachycardia in patients with severe CHF results in a three-fold increase in sudden death compared to those without tachycardia (Bigger, J. T., Jr. [1987] Circulation 75(suppl.IV):28). Because of the high prevalence of sudden unexpected death in patients with CHF, there has been a growing interest in the prognostic significance of arrhythmias in these patients.

Several compounds have been used in the management of cardiac arrhythmias in patients with congestive heart failure. Unfortunately, anti-arrhythmic drug therapy has been disappointing. The efficacy of anti-arrhythmic drugs markedly decreases as left ventricular function declines, such that only a small fraction of patients with CHF are responsive to anti-arrhythmic therapy. No anti-arrhythmic drug has prevented sudden death in patients with CHF and there is even a question of increased mortality associated with certain anti-arrhythmic drugs (the CAST investigators [1989] N. Engl. J. Med. 321:406).

Scientists define tachycardia and ventricular fibrillation as being of multiple nature. It now seems clear, and is accepted in the art, that re-entry is the underlying mechanism to most sustained arrhythmias. Prolonging ventricular repolarization as a means of preventing ventricular arrhythmias has consequently received renewed attention. This points to Class-III agents as drugs of choice in the treatment of arrhythmias. A Class-III agent, as referred to herein, is an agent that is classified as such in the Vaughan-Williams classification of anti-arrhythmic drugs. A Class-III agent exerts its primary anti-arrhythmic activity by prolonging cardiac action potential duration (APD), and thereby the effective refractory period (ERP), with no effect on conduction. These electrophysiological changes, which are brought about by blockade of cardiac potassium channels, are well known in the art. Because the blockade of cardiac potassium channels is not associated with depression of the contractile function of the heart, Class-III agents are particularly attractive for use in patients with CHF. Unfortunately, the existing Class-III agents are limited in their utility by additional pharmacological activities, lack of good oral bioavailability, or a poor toxicity profile. Two Class III agents currently marketed are bretylium (i.v. only) and amiodarone (i.v. and p.o.).

Amiodarone is an anti-arrhythmic agent having vasodilator properties that may benefit patients with severe heart failure. Amiodarone has been shown to improve survival of post- myocardial infarction patients with asymptomatic high-grade ventricular arrhythmias, and it proved efficacious in patients resistant to other anti-arrhythmic drugs without impairing left ventricular function. Cardioprotective agents and methods which employ amiodarone in synergistic combination with vasodilators and beta blockers have been described for use in patients with coronary insufficiency (U.S. Pat. No. 5,175,187). Amiodarone has also been described for reducing arrhythmias associated with CHF as used in combination with antihypertensive agents, e.g., (S)-1-[6-amino-2-[[hydroxy(4-phenylbutyl)phosphinyl]oxyl]-L- proline (U.S. Pat. No. 4,962,095) and zofenopril (U.S. Pat. No. 4,931, 464). However, amiodarone is a difficult drug to manage because of its numerous side effects, some of which are serious.

The most serious long-term toxicity of amiodarone derives from its kinetics of distribution and elimination. It is absorbed slowly, with a low bioavailability and relatively long half-life. These characteristics have clinically important consequences, including the necessity of giving loading doses, a delay in the achievement of full anti-arrhythmic effects, and a protracted period of elimination of the drug after its administration has been discontinued.

Amiodarone can also interact negatively with numerous drugs including aprindine, digoxin, flecainide, phenytoin, procainamide, quinidine, and warfarin. It also has pharmacodynamic interactions with catecholamines, diltiazem, propranolol, and quinidine, resulting in alpha- and beta-antagonism, sinus arrest and hypotension, bradycardia and sinus arrest, and torsades de pointes and ventricular tachycardias, respectively. There is also evidence that amiodarone depresses vitamin K-dependent clotting factors, thereby enhancing the anticoagulant effect of warfarin.

Numerous adverse effects limit the clinical applicability of amiodarone. Important side effects can occur including corneal microdeposits, hyperthyroidism, hypothyroidism, hepatic dysfunction, pulmonary alveolitis, photosensitivity, dermatitis, bluish discoloration, and peripheral neuropathy.

There is no Class-III agent presently marketed that can be used safely in patients with CHF. The cardiovascular drug market is the largest in any field of drug research, and an effective and safe Class-III anti-arrhythmic agent useful in patients with CHF is expected to be of substantial benefit. Therefore, a drug that could successfully improve the prognosis of CHF patients, but with a safety profile much improved over that of amiodarone, would be extremely useful and desired. Various analogs of amiodarone have been previously described (U.S. Pat. Nos. 6,372,783; 6,362,223; 6,316, 487; 6,130,240; 5,849,788; 5,440,054; and 5,364,880). The subject invention adds to this arsenal of compounds.

SUMMARY OF THE INVENTION

The invention comprises compounds of Formula 1:

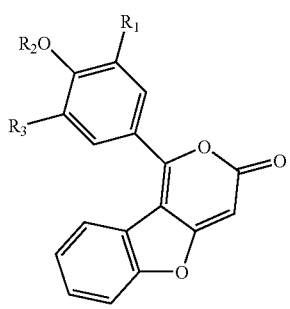

Formula 1 and hydrates, solvates, salts and tautomers thereof, wherein, $R_1$ is H or halogen;
$R_2$ is H or —$R_{10}$—$NR_{11}R_{12}$, wherein
$R_3$ is H or halogen;
$R_{10}$ is $C_1$-$C_6$ alkylene, and
$R_{11}$ and $R_{12}$ are independently H, $C_1$-$C_4$ alkyl.

The subject invention further comprises methods for making compounds of Formula 1, as well as for Formulae 2-4, which are described elsewhere herein.

The compounds of Formula 1 are useful in the synthesis of compounds according to Formula 5, which are useful in the treatment or prevention of cardiac arrhythmia and substantially reduce adverse effects associated with the administration of amiodarone, such as, for example, drug-drug interactions, corneal microdeposits, hyperthyroidism, hypothyroidism, hepatic dysfunction, pulmonary alveolitis, dermatitis, and peripheral neuropathy. As such, the subject invention further comprises methods for making compounds of Formula 5 for the treatment of prevention of cardiac arrhythmia using compounds of Formula 1.

The subject invention also comprises a method for making (R)-sec-butyl 2-(3-(4-(2-(diethylamino)ethoxy)-3,5-diiodobenzoyl)benzofuran-2-yl)acetate.

DETAILED DESCRIPTION OF THE INVENTION

The invention further comprises compounds of Formula 2:

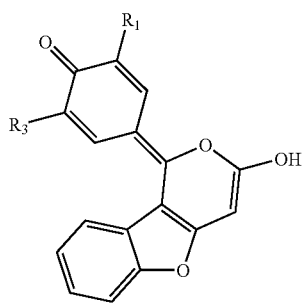

Formula 2 and hydrates, solvates, salts and tautomers thereof, wherein, $R_1$ is H or halogen, and
$R_3$ is H or halogen.

The invention further comprises a compound of Formula 3:

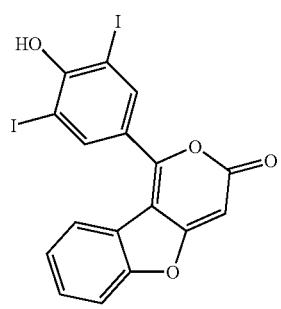

Formula 3 and hydrates, solvates, salts and tautomers thereof.

The invention further comprises a compound of Formula 4:

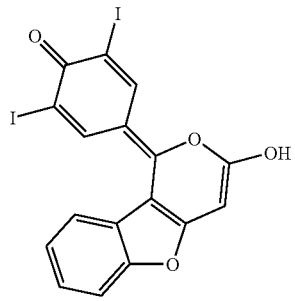

Formula 4 and hydrates, solvates, salts and tautomers thereof.

The invention further comprises compounds of Formula 5:

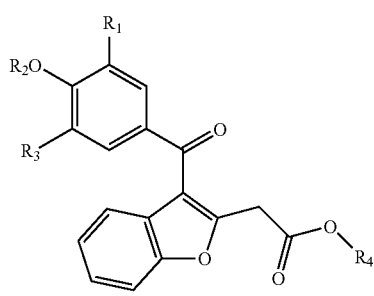

Formula 5 and hydrates, solvates, salts thereof, wherein, $R_1$ is H or halogen;
$R_2$ is H or —$R_{10}$—$NR_{11}R_{12}$; wherein,
$R_{10}$ is $C_1$-$C_6$ alkylene, and
$R_{11}$ and $R_{12}$ are independently H, $C_1$-$C_4$ alkyl;
$R_3$ is H or halogen; and
R is $C_1$-$C_6$ alkyl, such as, for example, methyl, ethyl, n-propyl, i-propyl, butyl, s-butyl, t-butyl, and the like. Alkyl moieties with one or more chiral centers are particularly contemplated, for example, S-2-butyl.

The invention further comprises methods for making compounds of Formulae 1-5.

The invention still further comprises methods of using compounds of Formulae 1-5.

The invention further comprises methods of making compounds of Table 1 and hydrates, solvates, salts thereof:

TABLE 1

| Structure | Chemical Name |
|---|---|
| 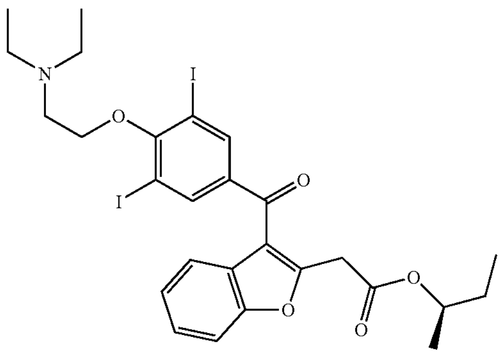 | (R)-sec-butyl 2-(3-(4-(2-(diethylamino)ethoxy)-3,5-diiodobenzoyl)benzofuran-2-yl)acetate |
| 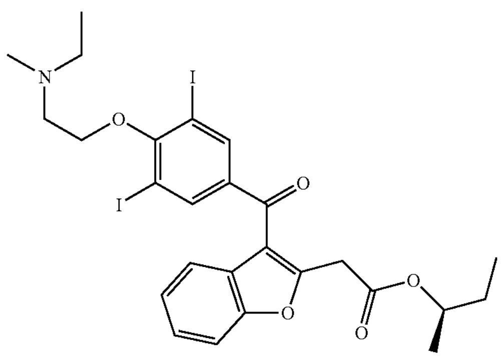 | (R)-sec-butyl 2-(3-(4-(2-(ethyl(methyl)amino)ethoxy)-3,5-diiodobenzoyl)benzofuran-2-yl)acetate |
| 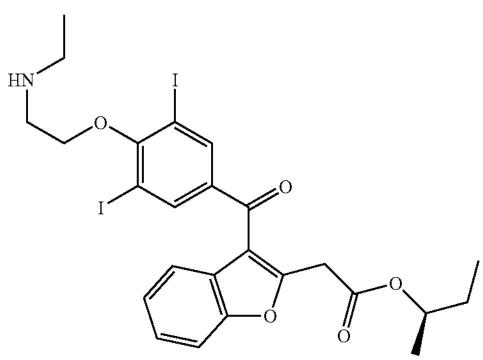 | (R)-sec-butyl 2-(3-(4-(2-(ethylamino)ethoxy)-3,5-diiodobenzoyl)benzofuran-2-yl)acetate |
| 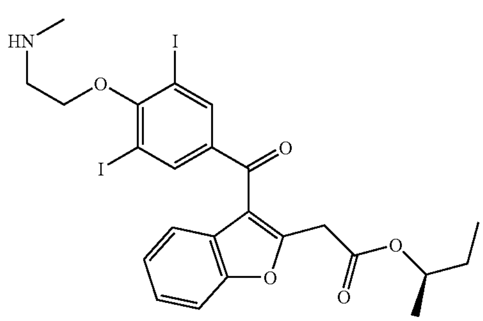 | (R)-sec-butyl 2-(3-(3,5-diiodo-4-(2-(methylamino)ethoxy)benzoyl)benzofuran-2-yl)acetate |

TABLE 1-continued

| Structure | Chemical Name |
|---|---|
| 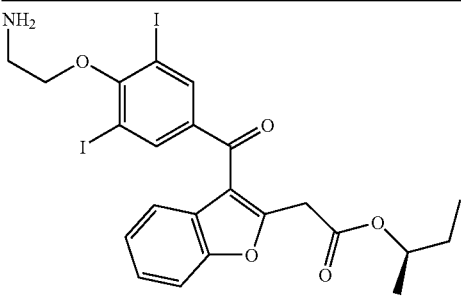 | (R)-sec-butyl 2-(3-(4-(2-aminoethoxy)-3,5-diiodobenzoyl)benzofuran-2-yl)acetate |
| 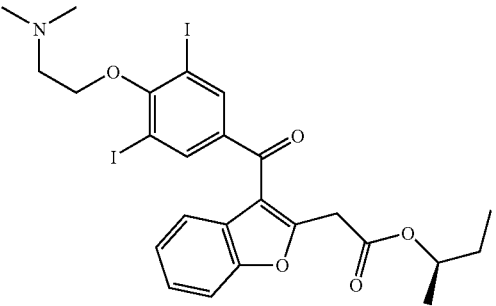 | (R)-sec-butyl 2-(3-(4-(2-(dimethylamino)ethoxy)-3,5-diiodobenzoyl)benzofurann-2-yl)acetate |

The subject invention provides methods for making compounds that are more susceptible to degradation by serum and/or cytosolic esterases than amiodarone, thus avoiding the adverse effects associated with metabolism by cytochrome P450.

Advantageously, the therapeutic compounds made according to methods of the subject invention are stable in storage but have a relatively short half-life in the physiological environment; therefore, the compounds of the subject invention can be used with a lower incidence of side effects and toxicity.

In certain aspects of the subject invention, methods for making therapeutic stereoisomeric compounds are provided that are useful in the treatment of cardiac arrhythmia and that contain an ester group, which is susceptible to degradation by esterases, thereby breaking down the compound and facilitating its efficient removal from the treated individual. In a preferred aspect, the therapeutic stereoisomeric compounds are metabolized by the Phase I drug detoxification system. Particularly, methods of producing and purifying such stereoisomeric compounds are taught. Methods of adding such ester moieties and of producing and purifying stereoisomers, are well known to the skilled artisan and can be readily carried out utilizing the guidance provided herein.

Definitions and Conventions

The definitions and explanations below are for the terms as used throughout this entire document including both the specification and the claims.

I. Conventions for Formulas and Definitions of Variables

The chemical formulas representing various compounds or molecular fragments in the specification and claims may contain variable substituents in addition to expressly defined structural features. These variable substituents are identified by a letter or a letter followed by a numerical sub- or superscript, for example, "$Z_1$" or "$Z^1$" or "$R_i$" where "i" is an integer. These variable substituents are either monovalent or bivalent. That is, they represent groups attached to the remainder of the molecule by one or two chemical bonds. Whether one or two bonds are present will be clear from the context to those of ordinary skill in the art. For example, a group Z, could represent a bivalent variable, as in $CH_3$—C($=Z_1$)H. As another example, groups $R_i$ and $R_j$ could represent monovalent variable substituents, as in $CH_3$—$CH_2$—C($R_i$)($R_j$)H. When chemical structures are drawn in a linear fashion, such as those above, variable substituents contained in parentheses are bonded to the atom immediately to the left of the variable substituent enclosed in parenthesis. When two or more consecutive variable substituents are enclosed in parentheses, each of the consecutive variable substituents is bonded to the immediately (i.e., first) preceding atom to the left that is not enclosed in parentheses. Thus, in the formula above, both $R_i$ and $R_j$ are bonded to the preceding carbon atom. Also, for any molecule with an established system of carbon atom numbering, such as steroids, these carbon atoms are designated as $C_i$, where "i" is the integer corresponding to the carbon atom number. For example, $C_6$ represents the 6 position or carbon atom number in the steroid nucleus as traditionally designated by those skilled in the art of steroid chemistry. "$C_i$" may refer to the ith carbon or a moiety comprising "i" carbon atoms. Which meaning is employed will be clear to those of ordinary skill in the art in the context of the usage.

Chemical structures or portions thereof drawn in a linear fashion represent atoms in a linear chain. The symbols "———" and "—" in general represents a bond between two atoms in the chain. Thus, $CH_3$—O—$CH_2$—CH($R_i$)—$CH_3$ and $CH_3$—O—$CH_2$—CH($R_i$)—$CH_3$, and combinations of "———" and "—" thereof, represent a 2-substituted-1-methoxypropane compound. Likewise, linear representations of a structure can be presented without "———" and/or "—" bonds. For instance, $CH_3OCH_2CH(R_i)CH_3$ also represents a 2-substituted-1-methoxypropane compound. In a similar fashion, the symbol "=" represents a double bond, e.g., $CH_2$=C($R_i$)—O—$CH_3$, and the symbol "≡" represents a triple bond, e.g., HC≡C———CH($R_i$)—$CH_2$—$CH_3$. Carbonyl groups are generally represented in one of four ways: CO, C(O), C(=O), or C=O either including or excluding flanking "——" bonds, with the first two representations being preferred for simplicity. Numbers immediately succeeding atoms in chemical formulas or portions thereof enumerate the number of preceding atoms or atom groups, as is standard practice in the chemical arts, whether in standard or subscript font. Thus, for example, a "C1-C8 alkyl" and a "$C_1$-$C_8$ alkyl" both describe an alkyl moiety of between 1 and 8 carbons in length.

A rigid cyclic (ring) structure for any compounds herein defines an orientation with respect to the plane of the ring for substituents attached to each carbon atom of the rigid cyclic compound. For saturated compounds which have two substituents attached to a carbon atom which is part of a cyclic system, —C($X_1$)($X_2$)— the two substituents may be in either an axial or equatorial position relative to the ring and may change between axial/equatorial. However, the position of the two substituents relative to the ring and each other remains fixed. While either substituent at times may lie in the plane of the ring (equatorial) rather than above or below the plane (axial), one substituent is always above the other relative to the plane of the ring as drawn in a particular orientation. In chemical structural formulas depicting such compounds, a substituent ($X_1$) which is "below" another substituent ($X_2$) will be identified as being in the alpha (α) configuration and is identified in text by a broken, dashed or dotted line attachment to the carbon atom, i.e., by the symbol " - - - " or " . . . ". The corresponding substituent attached "above" ($X_2$) the other ($X_1$) is identified in text as being in the beta (β) configuration and is indicated by an unbroken line attachment to the carbon atom. An example of $X_1$ being "below" $X_2$ is as follows: if $X_1$ is positioned equatorially, $X_2$ is positioned axially, "up" from the plane of the ring, out of the plane of the paper and toward the viewer of a 2-dimensional representation of the structure. An alternate example is when $X_2$ is positioned equatorially, $X_2$ is positioned axially, "down" from the plane of the ring, into the plane of the paper and away from the viewer of a 2-dimensional representation of the structure.

When a variable substituent is bivalent, the valences may be taken together or separately or both in the definition of the variable. For example, a variable $R_i$ attached to a carbon atom as —C(=$R_i$)— might be bivalent and be defined as oxo or keto (thus forming a carbonyl group (—CO—) or as two separately attached monovalent variable substituents α-$R_{i-j}$ and β-$R_{i-k}$, where "i" identifies the particular R group and "j" and "k" identifies the particular $R_i$. When a bivalent variable, $R_i$, is defined to consist of two monovalent variable substituents, the convention used to define the monovalent variables is of the form "α-$R_{i-j}$ and β-$R_{i-k}$" or some variant thereof. In such a case both α-$R_{i-j}$ and β-$R_{i-k}$ are attached to the carbon atom to give —C(α-$R_{i-j}$)(β-$R_{i-k}$)—. For example, when the bivalent variable $R_6$, —C(=$R_6$)—, is defined to consist of two monovalent variable substituents, the two monovalent variable substituents are α-$R_{6-1}$:β-$R_{6-2}$, giving —C(α-$R_{6-1}$)(β-$R_{6-2}$)—. Likewise, for the bivalent variable $R_{11}$, —C(=$R_{11}$)—, two monovalent variable substituents are α-$R_{11-1}$:β-$R_{11-2}$. For a ring substituent for which separate α and β orientations do not exist (e.g. due to the presence of a carbon-carbon double bond in the ring), and for a substituent bonded to a carbon atom which is not part of a ring the above convention is still used, but the α and β designations are omitted.

Just as a bivalent variable may be defined as two separate monovalent variable substituents, two separate monovalent variable substituents may be defined to together form a bivalent variable. For example, in the formula —$C_1$($R_i$)H—$C_2$($R_j$)H— ($C_1$ and $C_2$ define arbitrarily a first and second carbon atom, respectively), $R_i$ and $R_j$ may be defined to together form (1) a second bond between $C_1$ and $C_2$ or (2) a bivalent group such as oxa (—O—) and the formula thereby describes an epoxide.

The carbon atom content of variable substituents is indicated as follows: the carbon atom content of only each portion of the definition is indicated separately by enclosing the "$C_i$-$C_j$" designation in parentheses and placing it before the portion of the definition being defined. By this first convention, $C_2$-$C_4$ alkoxycarbonyl describes a group $CH_3$—$(CH_2)_n$—O—CO— where n is one, two or three. Similarly while both $C_2$-$C_6$ alkoxyalkyl and ($C_1$-$C_3$)alkoxy($C_1$-$C_3$)alkyl define alkoxyalkyl groups containing from 2 to 6 carbon atoms, the two definitions differ since the former definition allows either the alkoxy or alkyl portion alone to contain 4 or 5 carbon atoms while the latter definition limits either of these groups to 3 carbon atoms.

Where mandatory heteroatoms (via a "hetero" recitation without parentheses) or optional heteroatoms are introduced (via a "hetero" recitation inside parentheses, e.g., "(hetero)"), the numbering preferentially reflects the replacement of an existing carbon atom in the moiety with a heteroatom. Thus, while a general "$C_6$ alkyl" recitation comprises straight, branched and cyclic alkyl radicals with six carbons, a "$C_6$ heteroalkyl" recitation (or "$C_6$ (hetero)alkyl" in which a heteroatom is included) contains, in this example, five carbons, one having been replaced by a heteroatom.

It is to be understood that "a" as used herein includes both the singular and plural.

The general definitions used herein have the following meanings within the scope of the present invention.

II. Definitions:

All temperatures are in degrees Celsius unless otherwise specified.

TLC refers to thin-layer chromatography.

psi refers to pounds/$in^2$.

HPLC refers to high pressure liquid chromatography

Ac refers to acetyl (methylcarbonyl)

aq refers to aqueous

BFAA refers to benzofuran-2-yl-acetic acid

Bn refers to benzyl

BOC refers to 1,1-dimethylethoxy carbonyl and t-butoxycarbonyl, —CO—O—C($CH_3$)$_3$ c refers to concentration (g/mL, unless otherwise specified)

CDI refers to 1,1'-carbonyldiimidazole

Chromatography (column and flash chromatography) refers to purification/separation of compounds expressed as (support, eluent). It is understood that the appropriate fractions are pooled and concentrated to give the desired compound(s)

Conc. Refers to "concentrated." For example, "conc hydrochloric acid" or "conc HCl" refers to concentrated hydrochloric acid.

DCM refers to dichloromethane, or methylene chloride, or $CH_2Cl_2$ de refers to diastereomeric excess DMA refers to dimethylacetamide DME refers to dimethoxyethane DMF refers to N,N-dimethylformamide EA refers to ethyl acetate (EtOAc)

EDTA refers to ethylene diamine tetraacetic acid eq refers to equivalent

Et refers to ethyl

Ether refers to diethyl ether

EtOH refers to ethanol
g refers to grams
h refers to hours
$IC_{50}$ refers to the concentration of a compound that reduces (inhibits) enzyme activity by half
iso refers to an alkyl chain having the ending group 2-methylpropyl, i.e.—$CH(CH_3)_2$
L refers to liter
Min refers to minute
max refers to maximum
mg refers to milligram
mL refers to milliliter
mm refers to millimeter
mM refers to millimolar
mmol refers to millimole
mp refers to melting point
Me refers to methyl
mp refers to melting point
n refers to normal, i.e. unbranched, e.g. n-Pr is —$CH_2$—$CH_2$—$CH_3$ unless preceded by parentheses or brackets, e.g., —$(CH_2)_n$—, wherein n refers to a variable
N refers to normal
ng refers to nanogram
nm refers to nanometers
NMR refers to nuclear (proton) magnetic resonance spectroscopy, chemical shifts are reported in ppm (d) downfield from TMS
OD refers to optical density
pg refers to picogram
pM refers to picoMolar
RT refers to room temperature
t or tert refers to tertiary in an alkyl chain, e.g. t-butyl is —$C(CH_3)_3$ Tautomer refers to one of two or more structural isomers that exist in equilibrium and are readily converted from one isomeric form to another. Of the various types of tautomerism that are possible, two are commonly observed; keto-enol and ring-chain tautomerism. In keto-enol tautomerism, a simultaneous shift of electrons and a hydrogen atom occurs. In ring-chain tautomerism, an aldehyde group in a sugar chain molecule reacting with one of the hydroxy groups in the same molecule to give it a cyclic (ring-shaped) form. As one example, where R2 of Formula 1 is OH, the compound may undergo tautomerism:

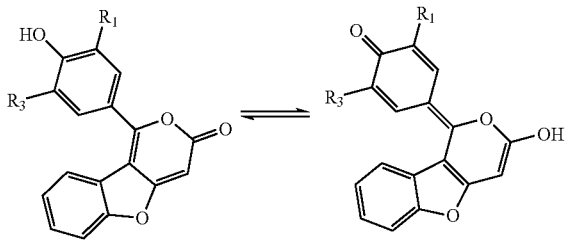

TEA refers to triethylamine
TFA refers to trifluoroacetic acid, $CF_3$—COOH
THF refers to tetrahydrofuran
Tol refers to toluene
UV refers to ultraviolet
μL=microliter
μM=micromolar (an expression of concentration in micromoles/liter)

Unless otherwise indicated, all functional group radicals (e.g., alkyl, aryl, cycloalkyl, etc.) are optionally substituted. Substituted functional group radicals are substituted with one or more substituents, unless indicated otherwise. Suitable substituents for substituted functional group radicals include, as non-limiting examples, $C_1$-$C_8$ (hetero)alkyl (i.e., the "alkyl" portion being inclusive of straight, branched and cyclic (hetero)alkyls and heteroatom-containing analogs), $C_1$-$C_8$ (hetero)alkoxy, halogen, hydroxy, cyano, nitro, amino, mono($C_1$-$C_8$)(hetero)alkylamino, di($C_i$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$ (hetero)alkenyl, $C_2$-$C_8$ (hetero)alkynyl, $C_1$-$C_8$ haloalkyl, $C_1$-$C_8$ haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$)(hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy(hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$) (hetero)alkyl and/or (hetero)aryl groups, amido, sulfamido, acetylene, amidino, and the like, attached at any available point on the compound.

Also unless otherwise indicated, all functional group radicals comprising a chain (e.g., alkyl, heteroalkyl, etc.) may be linear, branched or cyclized, unless otherwise specified.

Radical Definitions

As used herein, the terms "alkane" or "alkyl"—alone or in combination with other radicals and/or substituents—refer to a saturated hydrocarbon-derived radical containing from 1 to about 20, preferably 1 to about 15, carbon atoms (unless specifically defined). "Alkyl" refers to a straight chain alkyl, branched alkyl or cycloalkyl radicals and radical substituents (i.e., substitutions). Preferably, straight or branched alkyl groups contain from 1 to about 15, more preferably 1 to about 8, even more preferably 1 to about 6, yet more preferably 1 to about 4 and more preferably 1 to about 2, carbon atoms, such as methyl, ethyl, propyl, isopropyl, butyl, iso-, sec- and tert-butyl, pentyl, hexyl, heptyl, 3-ethylbutyl, and the like. Preferably, cycloalkyl groups are each independently monocyclic, bicyclic or polycyclic ring systems of 3 to about 10, more preferably 3 to about 6, ring atoms per ring, such as cyclopropyl, cyclobutyl, cyclopentyl, cyclohexyl, and the like. Alkyl also includes straight chain or branched alkyl group(s) that contains or is interrupted by a cycloalkyl portion. The straight chain or branched (both independently substituted or unsubstituted as described below) alkyl group is attached at any available point to produce a stable compound. Examples of this include, but are not limited to, 4-(isopropyl)-cyclohexylethyl or 2-methyl-cyclopropylpentyl. "Alkyl" also includes straight chain alkyl, branched alkyl, and/or cycloalkyl group defined previously, independently substituted with 1 to about 6 groups or substituents of $C_1$-$C_8$(hetero) alkyl (i.e., the "alkyl" portion being inclusive of straigh, branched and cyclic (hetero)alkyls and heteroatom-containing analogs), $C_1$-$C_8$(hetero)alkoxy, halogen, hydroxy, cyano, nitro, amino, mono($C_1$-$C_8$)(hetero)alkylamino, di($C_1$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$(hetero)alkenyl, $C_2$-$C_8$(hetero)alkynyl, $C_1$-$C_8$ haloalkyl, $C_1$-$C_8$ haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$)(hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy(hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$)(hetero)alkyl and/or (hetero)aryl groups, amido, sulfamido, acetylene, amidino, and the like, attached at any available point on the compound.

As used herein, the term "heteroalkyl"—alone or in combination with other radicals and/or substituents—refers to an "alkyl" as defined herein wherein one or more heteroatoms selected from N, O, S and P are substituted for one or more atoms of the "alkyl" moiety. For example, a "$C_8$ heteroalkyl" can be exemplified by —$C_4$—N—$C_3$—, —$C_3$—N—$C_4$—, —$C_2$—N—$C_5$—, and the like. Heteroalkyl groups are unsubstituted or substituted with, for example, $C_1$-$C_8$(hetero)alkyl (i.e., the "alkyl" portion being inclusive of straight, branched and cyclic (hetero)alkyls and heteroatom-containing analogs), $C_1$-$C_8$ (hetero)alkoxy, halogen, hydroxy, cyano, nitro, amino, mono($C_1$-$C_8$)(hetero)alkylamino, di($C_1$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$(hetero)alkenyl, $C_2$-$C_8$(hetero)alkynyl, $C_1$-$C_8$ haloalkyl, $C_1$-$C_8$ haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$)(hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy(hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$)(hetero)alkyl and/or (hetero)aryl groups, amido, sulfamido, acetylene, amidino, and the like, attached at any available point on the compound.

As used herein, the terms "alkene" and "alkenyl"—alone or in combination with other radicals and/or substituents—refer to a straight, branched, or cyclic (or combination of linear or branched with cyclic) hydrocarbon containing 2 to about 20, preferably 2 to about 17, more preferably 2 to about 10, even more preferably 2 to about 8, most preferably 2 to about 4, carbon atoms and at least one, preferably 1 to about 3, more preferably 1 to about 2, most preferably one, carbon to carbon double bond. In the case of a cycloalkenyl group, conjugation of more than one carbon to carbon double bond is not such as to confer aromaticity to the ring. Carbon to carbon double bonds are either contained within a cycloalkyl portion (thereby making it a "cycloalkenyl"), with the exception of cyclopropyl, or within a straight chain or branched portion. Examples of alkenyl groups include ethenyl, propenyl, isopropenyl, butenyl, cyclohexenyl, cyclohexenylalkyl and the like. "Alkene" and "alkenyl" refer to substituted and unsubstituted straight chain alkenyl, branched alkenyl or cycloalkenyl group defined previously, independently substituted with 1 to about 10 groups or substituents of, for example, $C_1$-$C_8$(hetero)alkyl (i.e., the "alkyl" portion being inclusive of straight, branched and cyclic (hetero)alkyls and heteroatom-containing analogs), $C_1$-$C_8$(hetero)alkoxy, halogen, hydroxy, cyano, nitro, amino, mono($C_1$-$C_8$)(hetero)alkylamino, di($C_1$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$(hetero)alkenyl, $C_2$-$C_8$(hetero)alkynyl, $C_1$-$C_8$ haloalkyl, $C_1$-$C_8$ haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$)(hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy(hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$)(hetero)alkyl and/or (hetero)aryl groups, amido, sulfamido, acetylene, amidino, and the like, attached at any available point on the compound.

As used herein, the terms "heteroalkene" and "heteroalkenyl"—alone or in combination with other radicals and/or substituents—refer to "alkene" and "alkenyl" groups as defined herein wherein one or more heteroatoms selected from N, O, S and P are substituted for one or more atoms of an "alkene" or "alkenyl" moiety. For example, a "$C_8$ heteroalkenyl" can be exemplified by —$C_1$=$C_3$—N—$C_3$—, —$C_2$=$C_2$—N—$C_4$—, —$C_2$—N—$C_2$=$C_3$—, and the like. Heteroalkenyl and heteroalkene groups can optionally be unsubstituted or substituted with, for example, $C_1$-$C_8$(hetero)alkyl (i.e., the "alkyl" portion being inclusive of straight, branched and cyclic (hetero)alkyls and heteroatom-containing analogs), $C_1$-$C_8$(hetero)alkoxy, halogen, hydroxy, cyano, nitro, amino, mono($C_1$-$C_8$)(hetero)alkylamino, di($C_1$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$(hetero)alkenyl, $C_2$-$C_8$(hetero)alkynyl, $C_1$-$C_8$ haloalkyl, $C_1$-$C_8$ haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$) (hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy(hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$)(hetero)alkyl and/or (hetero)aryl groups, amido, sulfamido, acetylene, amidino, and the like, attached at any available point on the compound.

As used herein, the terms "alkyne" or "alkynyl"—alone or in combination with other radicals and/or substituents—refer to a straight or branched hydrocarbon containing 2 to about 20, preferably 2 to about 17, more preferably 2 to about 10, even more preferably 2 to about 8, most preferably 2 to about 4, carbon atoms containing at least one, preferably one, carbon to carbon triple bond. Examples of alkynyl groups include ethynyl, propynyl, butynyl and the like. A substituted alkynyl refers to the straight chain alkynyl or branched alkenyl defined previously, independently substituted with 1 to about 10 groups or substituents of, for example, $C_1$-$C_8$(hetero)alkyl (i.e., the "alkyl" portion being inclusive of straight, branched and cyclic (hetero)alkyls and heteroatom-containing analogs), $C_1$-$C_8$(hetero)alkoxy, halogen, hydroxy, cyano, nitro, amino, mono($C_1$-$C_8$)(hetero)alkylamino, di($C_1$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$(hetero)alkenyl, $C_2$-$C_8$(hetero)alkynyl, $C_1$-$C_8$ haloalkyl, $C_1$-$C_8$ haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$) (hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy(hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$)(hetero)alkyl and/or (hetero)aryl groups, amido, sulfamido, acetylene, amidino, and the like, attached at any available point on the compound.

As used herein, the terms "heteroalkyne" and "heteroalkynyl"—alone or in combination with other radicals and/or substituents—refer to "alkyne" and "alkynyl" groups as defined herein wherein one or more heteroatoms selected from N, O, S and P are substituted for one or more atoms of an "alkyne" or "alkynyl" moiety. For example, a "$C_8$ heteroalkynyl" can be exemplified by —C≡$C_3$—N—$C_3$—, —$C_2$≡$C_2$—N—$C_4$—, —$C_2$—N—$C_2$≡$C_3$—, and the like. Heteroalkynyl and heteroalkyne groups can optionally be unsubstituted or substituted with, for example, $C_1$-$C_8$(hetero)alkyl (i.e., the "alkyl" portion being inclusive of straight, branched and cyclic (hetero)alkyls and heteroatom-containing analogs), $C_1$-$C_8$(hetero)alkoxy, halogen, hydroxy, cyano, nitro, amino, mono($C_1$-$C_8$)(hetero)alkylamino, di($C_1$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$(hetero)alkenyl, $C_2$-$C_8$(hetero)alkynyl, $C_1$-$C_8$haloalkyl, $C_1$-$C_8$haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$) (hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy(hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$)(hetero)alkyl and/or (hetero)aryl groups, amido, sulfamido, acetylene, amidino, and the like, attached at any available point on the compound.

As used herein, the term "alkoxy"—alone or in combination with other radicals and/or substituents—refers to an alkyl group of indicated number of carbon atoms attached to the parent molecular moiety through an oxygen bridge. Examples of alkoxy groups include, for example, methoxy, ethoxy, propoxy and isopropoxy.

As used herein, the term "haloalkoxy"—alone or in combination with other radicals and/or substituents—refers to an alkoxy group substituted with at least one halogen atom and optionally further substituted with at least one additional halogen atom, where each halogen is independently F, Cl, Br or I. Preferred halogens are F or Cl. Preferred haloalkoxy groups contain 1-6 carbons, more preferably 1-4 carbons, and still more preferably 1-2 carbons. "Haloalkoxy" includes perhaloalkoxy groups, such as $OCF_3$ or $OCF_2CF_3$.

As used herein, the term "aryl"—alone or in combination with other radicals and/or substituents—refers to an aromatic carbocyclic group having a single ring (e.g., phenyl) that is optionally fused or otherwise attached to other aromatic hydrocarbon rings or non-aromatic hydrocarbon rings. "Aryl" includes multiple condensed rings in which at least one is aromatic, (e.g., 1,2,3,4-tetrahydronaphthyl, naphthyl), wherein each ring is optionally mono-, di-, or trisubstituted with the groups identified below. Preferred aryl groups of the present invention are phenyl, 1-naphthyl, 2-naphthyl, indanyl, indenyl, dihydronaphthyl, fluorenyl, tetralinyl or 6,7,8,9-tetrahydro-5H-benzo[a]cycloheptenyl. More preferred are phenyl, biphenyl, and naphthyl. Most preferred is phenyl. The aryl groups herein are optionally substituted in one or more substitutable positions with various groups. For example, such aryl groups are optionally substituted with, for example, $C_1$-$C_8$(hetero)alkyl (i.e., the "alkyl" portion being inclusive of straight, branched and cyclic (hetero)alkyls and heteroatom-containing analogs), $C_1$-$C_8$(hetero)alkoxy, halogen, hydroxy, cyano, nitro, amino, mono($C_1$-$C_8$)(hetero)alkylamino, di($C_1$-$C_8$)(hetero)alkylamino, mono($C_1$-$C_8$)(hetero)arylamino, di($C_1$-$C_8$)(hetero)arylamino, ($C_1$-$C_8$)(hetero)aryl-($C_1$-$C_8$)(hetero)alkylamino, $C_2$-$C_8$(hetero)alkenyl, $C_2$-$C_8$(hetero)alkynyl, $C_1$-$C_8$haloalkyl, $C_1$-$C_8$haloalkoxy, amino($C_1$-$C_8$)(hetero)alkyl, mono($C_1$-$C_8$)(hetero)alkylamino($C_1$-$C_8$)(hetero)alkyl, di($C_1$-$C_8$)(hetero)alkylamino($C_1$-$C_8$)(hetero)alkyl, =O, thiol, ($C_1$-$C_8$)(hetero)alkylthio, (hetero)aryl, (hetero)aryloxy, (hetero)aryl($C_1$-$C_8$)(hetero)alkyl, ($C_1$-$C_8$)(hetero)alkyl(hetero)aryl, (hetero)aryl($C_1$-$C_8$)(hetero)alkoxy, ($C_1$-$C_8$)(hetero)alkylcarbonyl, (hetero)arylcarbonyl, ($C_1$-$C_8$)(hetero)alkyloxycarbonyl, (hetero)aryloxycarbonyl, ($C_1$-$C_8$)(hetero)alkylcarbonyloxy, (hetero)arylcarbonyloxy, ($C_1$-$C_8$)(hetero)alkyloxycarbonyl($C_1$-$C_8$)(hetero)alkyl, ($C_1$-$C_8$)(hetero)alkylcarbonyloxy($C_1$-$C_8$)(hetero)alkyl, (hetero)aryloxycarbonyl($C_1$-$C_8$)(hetero)alkyl, (hetero)arylcarbonyloxy($C_1$-$C_8$)(hetero)alkyl, (hetero)aryloxycarbonyl($C_1$-$C_8$)(hetero)aryl, (hetero)arylcarbonyloxy (hetero)aryl, ($C_1$-$C_8$)(hetero)alkylthio, ($C_1$-$C_8$)(hetero)alkylsulfinyl, ($C_1$-$C_8$)(hetero)alkylsulfonyl, (hetero)acyloxy, aminosulfonyl optionally N-mono- or N,N-di-substituted with ($C_1$-$C_8$)(hetero)alkyl and/or (hetero)aryl groups, ($C_1$-$C_8$)(hetero)alkylsulfonylamino, (hetero)arylsulfonylamino, ($C_1$-$C_8$)(hetero)alkylcarbonylamino, (hetero)arylcarbonylamino, urea optionally substituted with ($C_1$-$C_8$)(hetero)alkyl and/or (hetero)aryl groups, amido, sulfamido, acetylene, amidino, and the like, attached at any available point on the compound.

As used herein, the terms "halo" or "halogen"—alone or in combination with other radicals and/or substituents—refers to all halogens, that is, chloro (Cl), fluoro (F), bromo (Br), iodo (I).

As used herein, the term "hydroxyl"—alone or in combination with other radicals and/or substituents—refers to the group —OH.

As used herein, the terms "thiol," "thio" or "mercapto"—alone or in combination with other radicals and/or substituents—refer to the group —SH.

As used herein, the term "alkylthio"—alone or in combination with other radicals and/or substituents—refers to the group —SR, as well as to —S(O)$_{n=1-2}$—R (i.e., sulfinyl and sulfonyl groups), where R is, for example, alkyl, (hetero)aryl, and (hetero)arylalkyl as defined herein.

As used herein, the term "amino"—alone or in combination with other radicals and/or substituents—refers to the group NRR', where R and R' may independently be, for example, hydrogen, (hetero)alkyl, (hetero)alkenyl, (hetero)alkynyl, and acyl, as defined herein, all of which (other than H) are optionally substituted.

As used herein, the term "amido"—alone or in combination with other radicals and/or substituents—refers to the group —C(O)NRR', where R and R' may independently be, for example, hydrogen, (hetero)alkyl, (hetero)cycloalkyl, (hetero)alkenyl, (hetero)alkynyl, (hetero)aryl, and acyl, as defined herein, all of which (other than H) are optionally substituted.

As used herein, the term "carboxyl"—alone or in combination with other radicals and/or substituents—refers to the group —C(O)OR, where R can be, for example, hydrogen, (hetero)alkyl, (hetero)cycloalkyl, (hetero)alkenyl, (hetero)alkynyl, (hetero)aryl, and acyl, as defined herein, all of which (other than H) are optionally substituted.

As used herein, the term "acyl"—alone or in combination with other radicals and/or substituents—refers to groups —C(O)R, where R can be, for example, hydrogen, (hetero)alkyl, (hetero)cycloalkyl, (hetero)alkenyl, (hetero)alkynyl, and (hetero)aryl, as defined herein, all of which (other than H) are optionally substituted.

As used herein, the term "pharmaceutically acceptable salts" or "a pharmaceutically acceptable salt thereof" refer to salts prepared from pharmaceutically acceptable non-toxic acids or bases including inorganic acids and bases and organic acids and bases. Since the compound of the present invention is basic, salts may be prepared from pharmaceutically acceptable non-toxic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. Furthermore, the term salt as used herein also includes coordination complexes between ionic compounds of the invention and one or more counterions. In the most preferred aspect, the compounds of Formula 5 are administered as the free base or as a tartrate or mono or dihydrochloride salt.

As used herein, the terms "treatment" and "treating" encompass prophylactic administration of the compound or a pharmaceutical composition comprising the compound ("prophylaxis") as well as remedial therapy to reduce, inhibit, or eliminate a disease or disorder mentioned herein. Prophylactic administration is intended for prevention of disorders in a subject that is at risk of having or suffering from one or more disorders mentioned herein. Thus, as used herein, the term "treatment", or a derivative thereof, contemplates partial or complete inhibition of the stated disease state, when an active ingredient of the invention is administered prophylactically or following the onset of the disease state for which such active ingredient of the is administered. "Prophylaxis" refers to administration of the active ingredient(s) to a mammal to protect the mammal from any of the disorders set forth herein, as well as others.

The term "therapeutically effective amount" refers to an amount necessary to achieve a derived therapeutic effect such as a reduction or elimination of arrhythmic events or the severity or longevity thereof.

A "mammal" may be, for example, a mouse, rat, pig, horse, rabbit, goat, cow, cat, dog, or human. In a preferred aspect, the mammal is a human.

The term "individual(s)" is defined as a single mammal to which is administered a compound of the present invention. The mammal may be, for example, a mouse, rat, pig, horse, rabbit, goat, cow, cat, dog, or human. In a preferred aspect, the individual is a human.

A radical and its heteroatom-substituted version (e.g., aryl and heteroaryl; the "hetero" substituent comprising one or more heteroatoms like, for example, N, O, S, and P) can be referred to together with a parenthetical (hetero) prefix. For example, "(hetero)aryl" refers to both aryl and heteroaryl radicals as they are defined herein. Further, because each radical definition also includes optional substitutions and, where appropriate, straight, branched and/or cyclic character (e.g., (hetero)alkyl and (hetero)alkenyl radicals, and others, can possess straight-chained, branched and/or cycloalkyl/cycloalkenyl character), reference to (hetero)radicals (e.g., "(hetero)aryl" and "(hetero)alkyl") refers to radicals that optionally contain one or more heteroatoms and, where appropriate, can contain straight-chained, branched, and/or cyclical character (and combinations thereof as described herein). Likewise, chemical descriptions including combinations of (hetero)radicals (e.g., "(hetero)alkyl(hetero)aryloxycarbonyl") can refer to combinations of any of the characteristics contains each radical as described above. Thus, a "(hetero)alkyl(hetero)aryloxycarbonyl" moiety can refer to, for example, an optionally-substituted, linear, branched, and/or cyclic (hetero)alkyl-substituted, optionally-substituted (hetero)aryloxycarbonyl moiety. As (hetero)aryl radicals are optionally substituted as described in their definition, one or more additional substitutions beyond the specified (hetero)alkyl substitution(s) may be present. As an additional example, references to sequential combinations of the same radical (e.g., (hetero)alkyl(hetero)alkyloxy) also refers to all combinations of each radical. For instance, a (hetero)alkyl(hetero)alkyloxy radical can refer to, as one of many examples, a branched-chain alkyl-substituted, heterocyclic alkyloxy radical. However, a (hetero)alkyl(hetero)alkyloxy radical can also refer to, as another of many examples, a straight-chain alkyl-substituted, heterocyclic alkyloxy radical. Thus, each "(hetero)alkyl" radical in "(hetero)alkyl(hetero)alkyloxy" can have different characteristics, from containing one or more heteroatoms or no heteroatoms, to alkyl chains of different lengths and linear, branched or cyclic character, and the like. Similarly, using the previous example, each (hetero)alkyl radical can have the same general characteristics. For example, a (hetero)alkyl(hetero)alkyloxy radical can refer to a heterocyclic alkyl-substituted heterocyclic alkyloxy radical. However, the term "heterocyclic alkyl-substituted heterocyclic alkyloxy radicals" encompasses more than one specie (e.g., a $C_6$ versus a $C_8$ heterocyclic alkyl substituent). Thus, while general characteristics of identically-named sequential radicals may be the same, as in the immediately-previous example, the specific chemical definition of each radical need not be the same.

Combinations of these terms for functional group radicals are also used. Typically, the last term in the designation contains the radical that bonds to the remainder of the chemical structure. For example, "haloalkyl" refers to an alkyl radical substituted by a halogen, "cycloalkylalkyl" refers to alkyl radical substituted by a cycloalkyl, and alkylcycloalkyl" refers to a cycloalkyl radical substituted by an alkyl.

For simplicity, chemical moieties are defined and referred to throughout primarily as univalent chemical moieties (e.g., alkyl, aryl, etc.). Nevertheless, such terms are also used to convey corresponding multivalent moieties under the appropriate structural circumstances clear to those skilled in the art. For example, while an "alkyl" moiety generally refers to a monovalent group (e.g. $CH_3$—$CH_2$—), in certain circumstances a bivalent linking moiety can be "alkyl," in which case those skilled in the art will understand the alkyl to be a divalent group (e.g., —$CH_2$—$CH_2$—), which is equivalent to the term "alkylene." (Similarly, in circumstances in which a divalent moiety is required and is stated as being "aryl," those skilled in the art will understand that the term "aryl" refers to the corresponding divalent moiety, arylene.) All atoms are understood to have their normal number of valences for bond formation (i.e., 4 for carbon, 3 for N, 2 for O, and 2, 4, or 6 for S, depending on the oxidation state of the S).

EXAMPLES

Without further elaboration, it is believed that one skilled in the art can, using the preceding description, practice the present invention to its fullest extent. The following detailed examples describe how to prepare the various compounds (i.e., those encompassed by Formulae 1-4, as well as those encompassed by Formula 5, which are synthesized from Formulae 1-4) and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Preparations of the novel compounds of the present invention are illustrated in the following example, which is not, however, intended to be any limitation thereof.

Descriptions of reactions described herein may recite specific amounts of reagents or "parts by weight" and "mole fractions." References to "parts by weight" and "mole fractions" describe, for example, the mass and stoichiometric relationships between the reagents utilized in the reactions, based on an arbitrarily assigned standard. For example, in a reaction that calls for the use of 36 g (approximately 2 moles) of water, water may be chosen as a reference reagent. As a reference reagent, the amount of water used in mass and moles can be defined as, for example, 1 part by weight and 1× mole fraction. Thus, in the example of this paragraph, 36g of water is defined as 1 part by weight, and 2 moles of water is defined as 1× mole fraction. The choice of a reference reagent for a single reaction or in a reaction scheme is wholly arbitrary, as is the choice of the reference number for parts by weight and mole fraction, here having chosen "1" for each.

Thereinafter, the amounts of reagents can be described in terms relative to the water, or any other chosen reference reagent. For example, the use of 400 g (4.55 moles) of ethyl acetate (molecular weight=88 g) can be described as 400g/36g, or 11.1, parts by weight and 4.55 mole/2 mole, or 2.27×, mole fraction.

Example 1

Exemplary synthesis of 4-(4-Hydroxy-3,5-diiodo-phenyl)-3,9-dioxa-fluoren-2-one ("Enol-lactone")

Exemplary synthetic scheme:

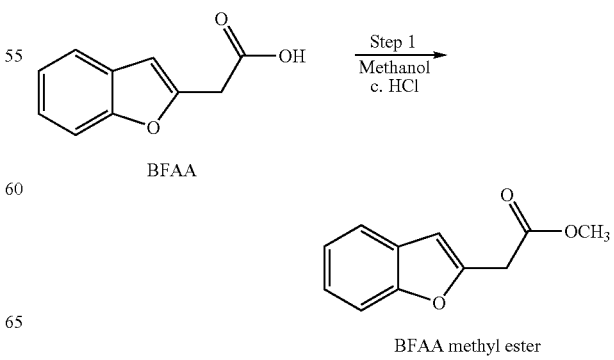

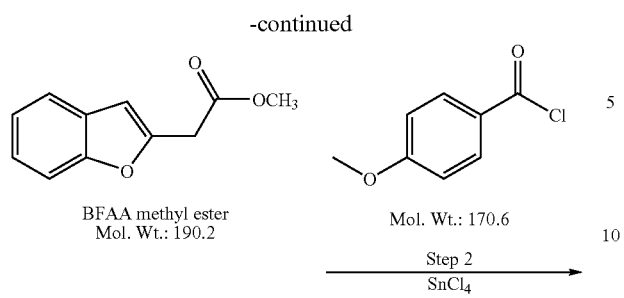
BFAA methyl ester
Mol. Wt.: 190.2
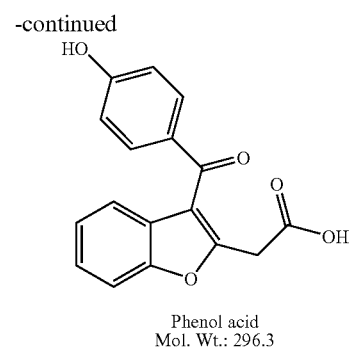
Mol. Wt.: 170.6
Step 2
SnCl₄
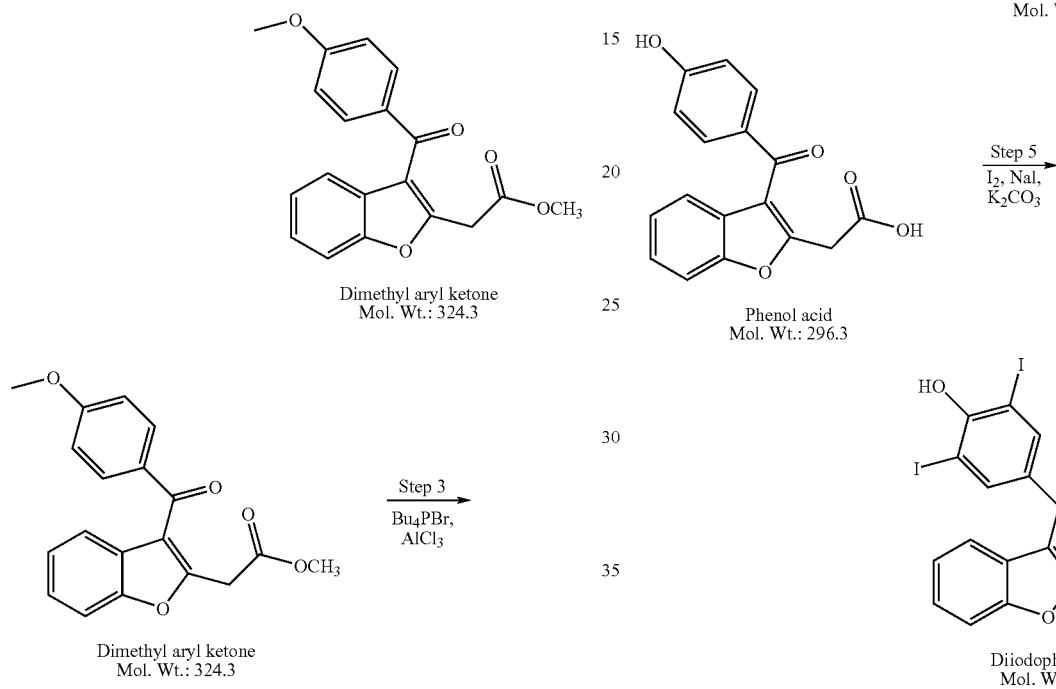
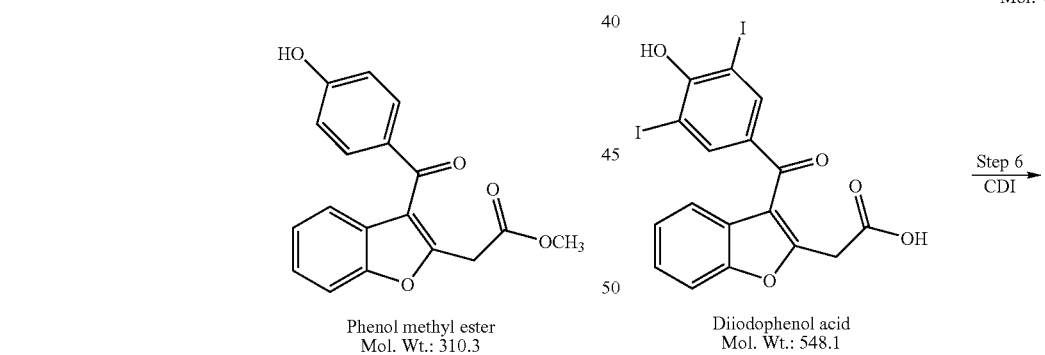
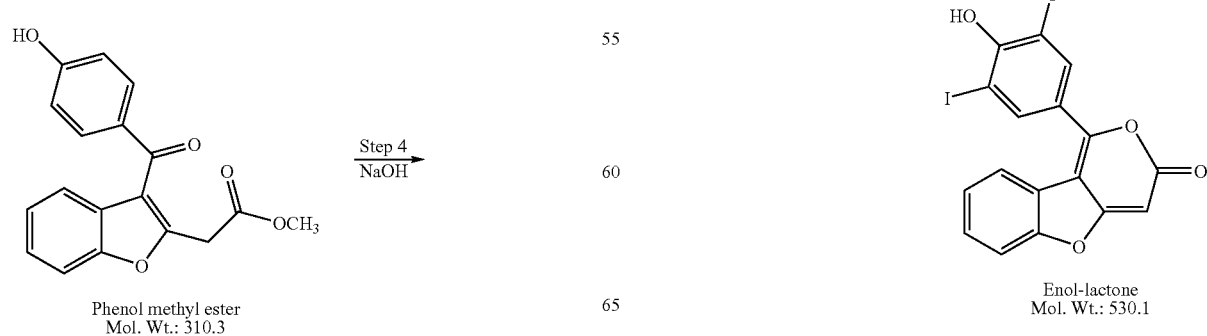

Exemplary step 1: benzofuran-2-yl-acetic acid methyl ester ("BFAA methyl ester") synthesis

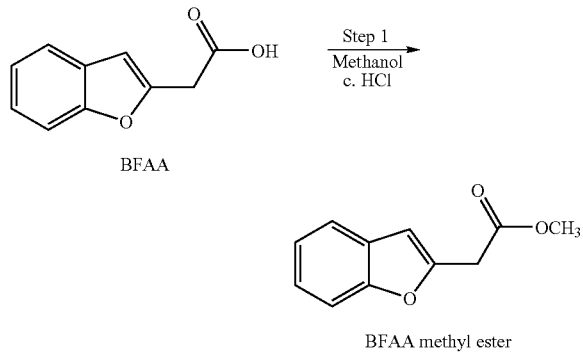

Benzofuran-2-yl-acetic acid (BFAA, defined as 1 part by weight; 1× mole fraction) was combined with toluene (approximately 4.3 parts by weight) and methanol (approximately 1.96 parts by weight) was added to form a solution. Concentrated (conc.) hydrochloric acid (approximately 0.28 parts by weight; 0.5× mole fraction) was added while controlling the temperature below about 25° C. and the reaction mixture was stirred for several hours. The reaction was quenched with excess aqueous sodium bicarbonate solution. The aqueous layer was separated and the organic layer was washed with aqueous sodium chloride solution. The aqueous layer was separated and the organic product layer was concentrated under vacuum. In this particular example. Heptane was added to the residue and concentrated under vacuum to yield the product BFAA methyl ester.

Exemplary step 2: [3-(4-Methoxy-benzoyl)-benzofuran-2-yl]-acetic acid methyl ester ("Dimethyl aryl ketone") synthesis

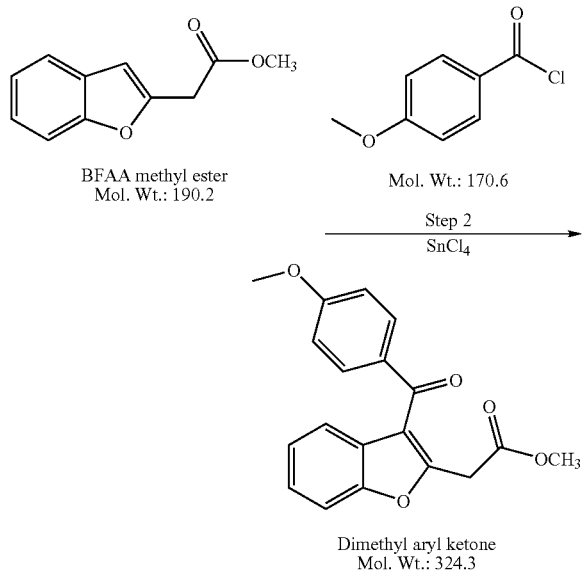

To the BFAA methyl ester from Step 1 (assumed 1× mole fraction) was added p-anisoyl chloride (approximately 1.08 parts by weight; 1.1× mole fraction), followed by methylene chloride (approximately 3.11 parts by weight). The mixture was stirred and cooled to about 0-5° C. Tin(IV) chloride (approximately 1.46 parts by weight) was added while controlling the batch temperature below about 10° C. The reaction was stirred at about 0-10° C. for about 3 hours then was warmed and stirred at about 20-25° C. for several hours. Methylene chloride was added and the reaction was cooled and quenched with 4% aqueous hydrochloric acid while controlling the temperature to below about 10° C. The organic layer was separated and washed with water. The organic layer was concentrated under vacuum and dried by distillation of more methylene chloride. The resulting product was dissolved in methylene chloride and transferred to a clean vessel.

Exemplary step 3: [3-(4-Hydroxy-benzoyl)-benzofuran-2-yl]-acetic acid methyl ester ("Phenol methyl ester") synthesis

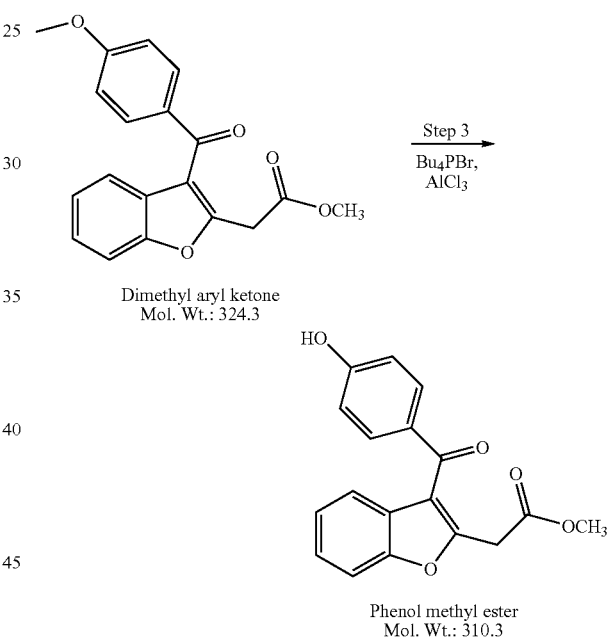

Aluminum chloride (approximately 2.08 parts by weight; 2.77× mole fraction) was combined with methylene chloride (approximately 8.88 parts by weight) to form a suspension. A solution of tetrabutylphosphonium bromide (approximately 1.69 parts by weight; 0.88× mole fraction) in methylene chloride (approximately 3.35 parts by weight) was added while controlling the temperature tonot more than about 30° C. One-half of the dimethyl aryl ketone solution prepared in step 2 (approximately 4.04 parts by weight solution, assumed 0.5× mole fraction) was added to the reaction vessel while controlling the temperature at not more than about 35° C. The reaction was stirred at about 30° C. for several hours. The reaction mixture was cooled to below about 10° C. and was then transferred into cold 14% aqueous hydrochloric acid solution (approximately 18.08 parts by weight) while controlling the temperature at below about 20° C. The organic layer was separated and washed several times with water. The organic layer was concentrated under vacuum. The residue was redissolved in, for example, ethyl acetate and washed with water and 10% aqueous sodium chloride solution. The washed ethyl acetate solution of phenol methyl ester product was drained to a clean vessel. The second half of the dimethyl aryl ketone starting material was converted to phenol methyl ester by this same procedure and workup. A total of approximately 19.96 parts by weight ethyl acetate solution of phenol methyl ester product was produced in the two exemplary runs described herein. The combined solution was concentrated under vacuum and, for example, n-heptane was added to precipitate the product. The product was collected at about 0° C. and dried on the filter with nitrogen. A yield of approximately 1.96 parts by weight of damp phenol methyl ester was obtained.

Exemplary step 4: [3-(4-Hydroxy-benzoyl)-benzofuran-2-yl]-acetic acid ("Phenol Acid") synthesis

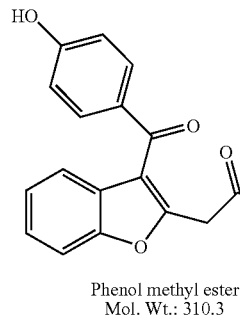

Phenol methyl ester
Mol. Wt.: 310.3

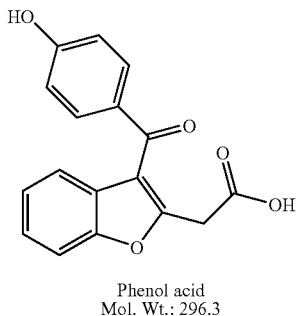

Phenol acid
Mol. Wt.: 296.3

The phenol methyl ester product of step 3 (approximately 1.96 parts by weight, assumed approximately 0.80× mole fraction) was suspended in water (approximately 8.46 parts by weight) in a reaction vessel. A solution of 9% aqueous sodium hydroxide (approximately 180 kg 6.92 parts by weight, 2.70× mole fraction moles) was added while controlling the temperature below about 40° C. After about 4 hours at about 10-30° C., the reaction mixture was washed with methylene chloride. The aqueous product layer was cooled and acidified with conc. hydrochloric acid (approximately 1.5 parts by weight, 2.64× mole fraction) while controlling the temperature below about 10° C., which caused the product to precipitate. The product was extracted into an organic, for example, ethyl acetate, and the aqueous layer was separated. The organic product layer was washed with water. The ethyl acetate solution of phenol acid product (approximately 8.54 parts by weight) was stored for use in exemplary step 5. A mass yield of 76% was assumed based on concentrating a sample to dryness.

Exemplary step 5: [3-(4-Hydroxy-3,5-diiodo-benzoyl)-benzofuran-2-yl]-acetic acid (Diiodophenol acid) synthesis

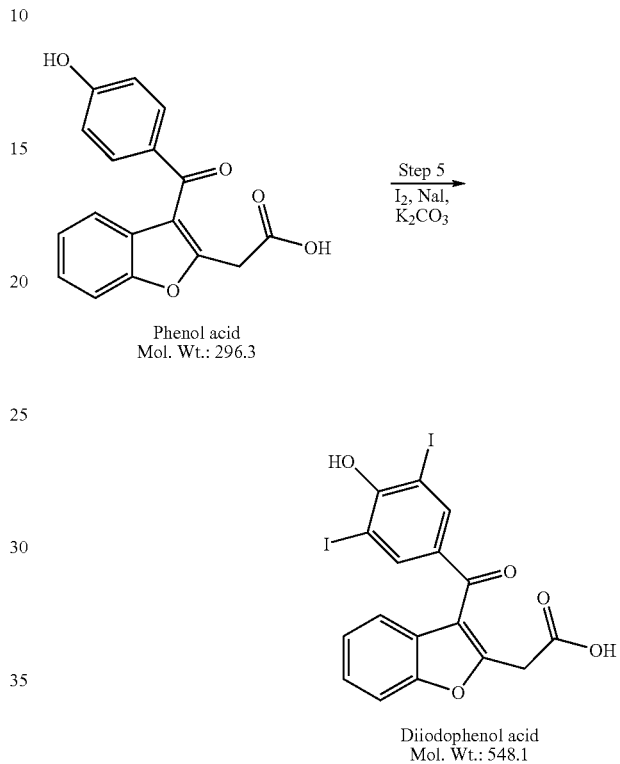

To a solution of potassium carbonate (approximately 1.08 parts by weight, 1.39× mole fraction) in water (approx. 13.08 parts by weight) was added about one-half the solution of phenol acid in ethyl acetate from step 4 4.31 parts by weight, approximately 0.30× mole fraction). The aqueous layer was separated and the waste organic layer was discarded. To the aqueous layer was added sodium iodide (approx. 0.017 parts by weight, 0.020× mole fraction). Iodine (approximately 1.27 parts by weight, 0.89 mole fraction) was added in three portions over about 3.5 hours at about 20-25° C. The reaction was stirred for about 3 more hours after the final iodine addition. The reaction mixture was washed with, for example, ethyl acetate and the aqueous product layer was separated. The aqueous layer was cooled and acidified with conc. hydrochloric acid (approximately 1.08 parts by weight, 1.89× mole fraction) to precipitate the product. The product suspension was held at about 35-40° C. for about 1 hour, followed by collecting the product in a filter. The solids were washed with water and then resuspended in water, collected on a filter, and washed with water. The water-wet cake was resuspended in toluene, and the solids were dried by distillation of the toluene-water azeotrope under vacuum at not more than about 45° C. The solids were then collected by filtration and washed with, for example, toluene. This process was repeated with the remaining half of the phenol acid starting material.

Exemplary step 6: 4-(4-Hydroxy-3,5-diiodo-phenyl)-3,9-dioxa-fluoren-2-one ("Enol-lactone") synthesis

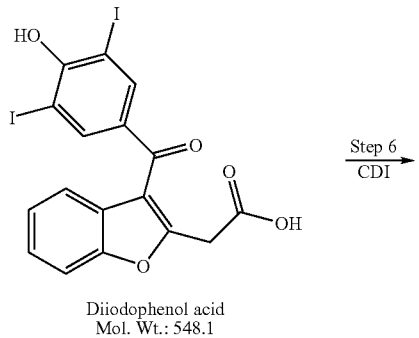

Diiodophenol acid
Mol. Wt.: 548.1

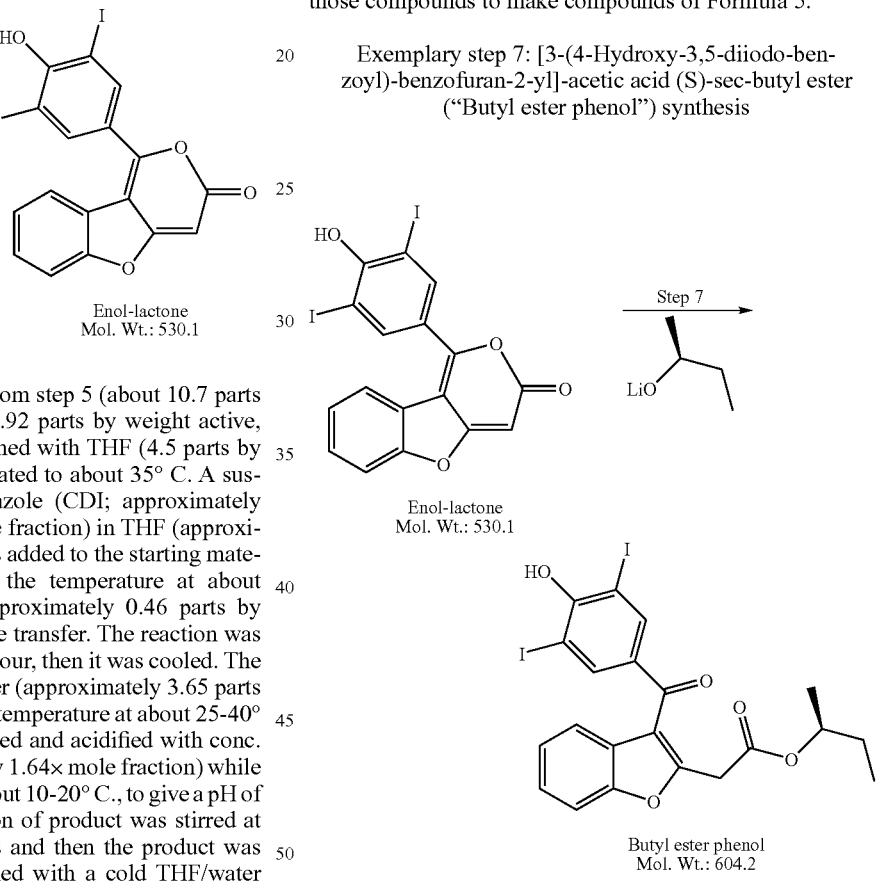

Enol-lactone
Mol. Wt.: 530.1

All the phenol acid wetcake from step 5 (about 10.7 parts by weight wet, approximately 1.92 parts by weight active, 0.61× mole fraction) was combined with THF (4.5 parts by weight), and the mixture was heated to about 35° C. A suspension of 1,1'-carbonyldiimidazole (CDI; approximately 0.88 parts by weight, 0.97× mole fraction) in THF (approximately 2.19 parts by weight) was added to the starting material solution while controlling the temperature at about 32-40° C. A rinse of THF (approximately 0.46 parts by weight) was used to complete the transfer. The reaction was held at about 35° C. for about 1 hour, then it was cooled. The reaction was quenched with water (approximately 3.65 parts by weight) while controlling the temperature at about 25-40° C. The reaction was further cooled and acidified with conc. hydrochloric acid (approximately 1.64× mole fraction) while controlling the temperature at about 10-20° C., to give a pH of about 3. The resulting suspension of product was stirred at about 0-5° C. for about 7 hours and then the product was collected by filtration and washed with a cold THF/water mixture. The product was dried in a vacuum dryer to yield approximately 1.60 parts by weight dry enol-lactone (about 0.53× mole fraction, 87%, uncorrected for assay). Representative enol-lactone physical data:

LCMS (M+: 531.03);

$^1$H-NMR: (400 MHz NMR): s: 6.22 (s, 1H); 7.25 (m, 1H); 7.46 (m, 3H); 8.11 (s, 1H); 10.46 (br. s, —OH);

$^{13}$C-NMR: 86.56; 88.14; 108.88; 111.74; 119.31; 120.81; 124.43; 126.18; 129.73; 138.51; 153.57; 156.84; 158.54; 161.79; 168.80.

The enol-lactone produced via the above exemplary steps (i.e., that of Formula 3, and of its tautomer, Formula 4) can be useful to generate a wide variety of compounds that can be used to reduce arrhythmias in individuals in need of such effects. The following exemplary steps, combined with the steps above, describe a method for synthesizing one member of the genus described by the generic formula, Formula 5, which is (R)-sec-butyl 2-(3-(4-(2-(diethylamino)ethoxy)-3,5-diiodobenzoyl)benzofuran-2-yl)acetate. Importantly, however, the methodology is applicable to a wide variety of compounds of the genus described by Formula 5. Other compounds described by the genus of Formula 5 can be made by, for example, substituting a different reacting species in step 5 (for example, $Fl_2$ or $Br_2$ for $I_2$), or deleting step 5 to retain the hydrogens on the "phenol acid", both synthetic routes generating compounds encompassed by Formula 1, and that of its tautomer, Formula 2. Additional cumulative or independent changes can be made to other steps in the described method, for example, the substitution of different alcohols in step 7 and/or different amines in step 8, below. Thus, the method of Example 1, and the disclosure provided elsewhere herein, can be used as a guide for one of skill in the art to make compounds of Formulae 1-4 and, in turn, use those compounds to make compounds of Formula 5.

Exemplary step 7: [3-(4-Hydroxy-3,5-diiodo-benzoyl)-benzofuran-2-yl]-acetic acid (S)-sec-butyl ester ("Butyl ester phenol") synthesis Enol-lactone
Mol. Wt.: 530.1

Butyl ester phenol
Mol. Wt.: 604.2

Enol-lactone (approximately 0.80 parts by weight, 0.26× mole fraction) was suspended in THF (approximately 4.31 parts by weight) and the suspension was cooled to about −5° C. In a separate reaction vessel, (S)-2-butanol (approximately 0.32 parts by weight, 0.77× mole fraction) was added to a 19% (wt/wt) solution of lithium tert-butoxide (approximately 1.50 parts by weight solution, 0.63× mole fraction) to produce a lithium (S)-2-butoxide solution. The resulting lithium (S)-2-butoxide solution was added into the cold enol-lactone suspension while controlling the temperature at below about 10° C. A THF rinse (approximately 1.85 parts by weight) was used to complete the transfer. The reaction was stirred for about 6 hours at about 0±5° C. The reaction was quenched using a dilute aqueous solution of hydrochloric acid and sodium chloride at below about 10° C. The aqueous layer was separated and the organic layer was washed with 25% aqueous sodium chloride solution. The organic layer was concentrated under vacuum. Ethyl acetate was added and concentrated under vacuum and the concentrate was filtered to remove any insoluble material. Methanol was added and the solution, which was then concentrated under vacuum. Additional methanol was added, and the solution was concentrated again. The concentrate was cooled to about −6° C. and the product was isolated by filtration and washed with cold methanol. The product was dried under vacuum at about 60° C. The yield was approximately 0.71 parts by weight dry butyl ester phenol product (here, about 78%).

As mentioned above, various alcohols can be substituted for the (s)-2-butanol described above. For example, methanol, ethanol, n-propanol, i-propanol, n-butanol, s-butanol, t-butanol, and the like. Further, alcohols with one or more chiral centers are described and contemplated, for example, (S)-2-butanol, (R)-2-butanol, (S)-3-pentanol and (R)-3-pentanol. In addition, halogenated alcohols can be utilized, for example, (S)-4,4,4-trifluorobutan-2-ol, (S)-4,4,4-trifluoro-3-(trifluoromethyl)butan-2-ol, (2S)-4,4,4-trifluoro-3-methylbutan-2-ol, (R)-4,4,4-trifluorobutan-2-ol, 4,4,4-trifluorobutan-2-ol, (S)-4,4,4-trichlorobutan-2-ol, and the like. Alcohols can be, for example, those according to HO—($C_1$-$C_6$)alkyl, and preferably HO—($C_3$-$C_4$)alkyl, alkyl as defined herein and therefore including, for example, straight-chain and branched alkyl moieties. Further, the alcohols can have one or more chiral centers and be optionally substituted as described herein. Preferred substitutions include one or more halogens.

Exemplary step 8: {(2S) butan-2-yl 2-[3-(4-{2-(diethylamino)ethoxy}-3,5-diiodobenzoyl)benzofuran-2-yl]acetate} (L) hydrogen tartrate salt (ATI-2042 Tartrate Salt) synthesis Step 8

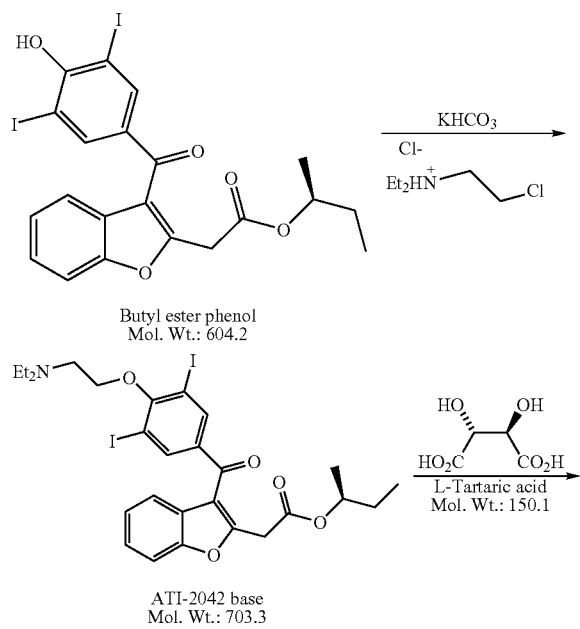

Butyl ester phenol
Mol. Wt.: 604.2

L-Tartaric acid
Mol. Wt.: 150.1

ATI-2042 base
Mol. Wt.: 703.3

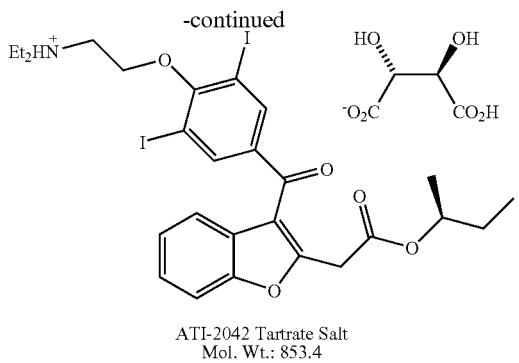

ATI-2042 Tartrate Salt
Mol. Wt.: 853.4

Butyl ester phenol (approximately 0.71 parts by weight, 0.21× mole fraction), potassium bicarbonate (approximately 0.35 parts by weight, 0.62× mole fraction), toluene (approximately 3.08 parts by weight) and USP purified water (approximately 0.35 parts by weight) were combined in a raction vessel. A solution of 2-(diethylamino)ethyl chloride hydrochloride (approximately 0.23 parts by weight, 0.23× mole fraction) in USP purified water (approximately 0.29 parts by weight) was added while controlling the temperature at about 25-30° C. Additional water (approximately 0.19 parts by weight) was added to complete the transfer. The reaction mixture was heated and stirred at about 50° C. for several hours. The batch was cooled to about 35° C. and filtered to remove insoluble material. The aqueous layer was separated and the organic layer was washed with aqueous sodium chloride solution. The organic layer was concentrated under vacuum to a residue that was redissolved in isopropanol.

A solution of L-tartaric acid (approximately 0.19 parts by weight, 0.22 × mole fraction) in USP purified water was added. After heating to about 45° C., additional USP purified water was added to give a solution that was polish-filtered. The product ATI-2042 tartrate salt solution was cooled and crystallized from the isopropanol/water mixture, collected on a filter, and dried under vacuum at about 20-35° C. to yield about 15 kg parts by weight product. The product was reslurried in isopropanol/water and collected on a filter.

As mentioned above, various halogenated amines and amine salts (e.g., hydrochloride) can be substituted for the 2-(diethylamino)ethyl chloride hydrochloride (2-chloro-N,N-diethylethanamine) described above. For example, 2-chloro-N-ethyl-N-methylethanamine hydrochloride or hydrobromide, 2-chloro-N,N-dimethylethanamine hydrochloride or hydrobromide, 2-chloro-N-methylethanamine hydrochloride or hydrobromide, 2-chloro-N-ethylethanamine hydrochloride or hydrobromide, 2-chloro-N-ethyl-N-methylethanamine hydrochloride or hydrobromide, 2-chloro-N,N-dimethylethanamine, 2-chloro-N-methylethanamine, 2-chloro-N-ethylethanamine and the like, may be substituted to generate an alternate amine moiety. Amines can be, for example, those according to X—$R_{10}$—$NR_{11}R_{12}$; wherein, X is a halogen; $R_{10}$ is $C_1$-$C_6$ alkyl (as defined herein, i.e., inclusive of, e.g., straight chain and branched alkyl); and $R_{11}$ and $R_{12}$ are independently H, $C_1$-$C_4$ alkyl as defined herein.

Example 2

Exemplary synthesis of 4-(4-Hydroxy-phenyl)-3,9-dioxa-fluoren-2-one ("Enol-lactone")

Exemplary synthetic scheme:

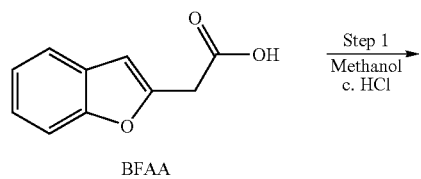

BFAA

Step 1
Methanol
c. HCl

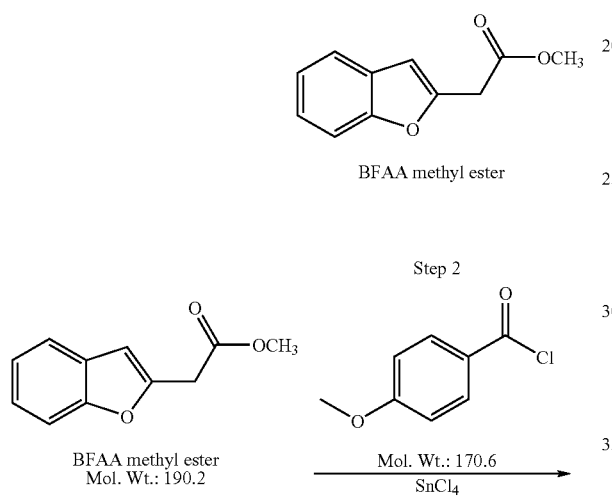

BFAA methyl ester

Step 2

BFAA methyl ester
Mol. Wt.: 190.2

Mol. Wt.: 170.6
SnCl₄

Dimethyl aryl ketone
Mol. Wt.: 324.3

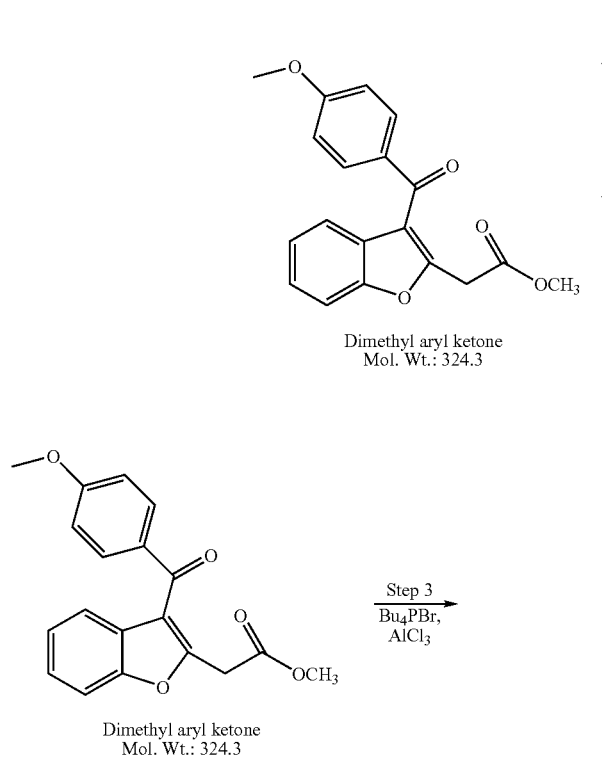

Dimethyl aryl ketone
Mol. Wt.: 324.3

Step 3
Bu₄PBr,
AlCl₃

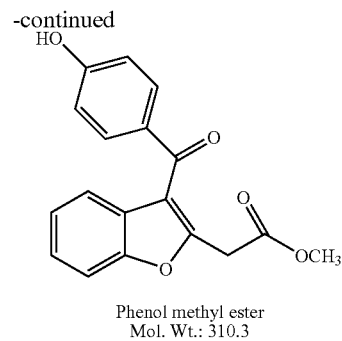

Phenol methyl ester
Mol. Wt.: 310.3

Exemplary steps 1 through 3 for Example 2 can be, for example, as listed in Example 1.

Exemplary step 4: [3-(4-Hydroxy-benzoyl)-benzofuran-2-yl]-acetic acid ("Phenol Acid") synthesis

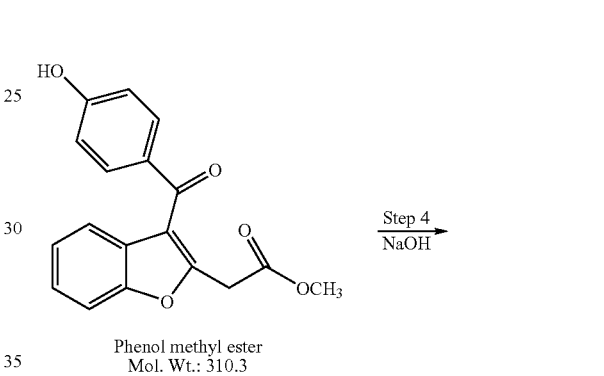

Phenol methyl ester
Mol. Wt.: 310.3

Step 4
NaOH

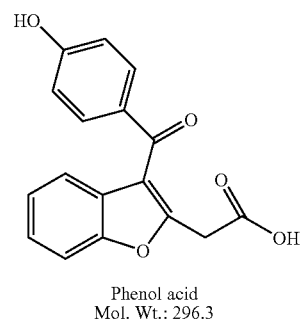

Phenol acid
Mol. Wt.: 296.3

The phenol methyl ester product of step 3 (approximately 1.96 parts by weight, assumed approximately 0.80× mole fraction) was suspended in water (approximately 8.46 parts by weight) in a reaction vessel. A solution of 9% aqueous sodium hydroxide (approximately 180 kg 6.92 parts by weight, 2.70× mole fraction moles) was added while controlling the temperature below about 40° C. After about 4 hours at about 10-30° C., the reaction mixture was washed with methylene chloride. The aqueous product layer was cooled and acidified with conc. hydrochloric acid (approximately 1.5 parts by weight, 2.64× mole fraction) while controlling the temperature below about 10° C., which caused the product to precipitate. The product was collected in a filter. The solids were washed with water and then resuspended in water, collected on a filter, and washed with water. The water-wet cake was resuspended in, for example, toluene, and the solids were dried by distillation of the toluene-water azeotrope under vacuum at not more than about 45° C. The solids were then collected by filtration and washed with, for example, toluene.

Exemplary step 5:
4-(4-Hydroxy-phenyl)-3,9-dioxa-fluoren-2-one synthesis

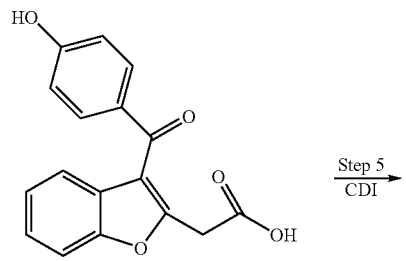
Phenol acid
Mol. Wt.: 296.3

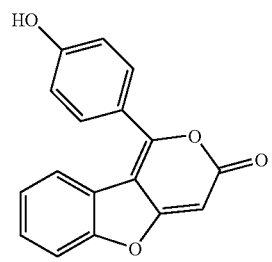

Enol-lactone
Mol. Wt.: 278.3

All the phenol acid wetcake from step 4 (about 11 parts by weight wet, approximately 2 parts by weight active, 0.6× mole fraction) was combined with THF (about 4.5 parts by weight), and the mixture was heated to about 35° C. A suspension of 1,1'-carbonyldiimidazole (CDI; approximately 0.88 parts by weight, 0.97× mole fraction) in THF (approximately 2.2 parts by weight) was added to the starting material solution while controlling the temperature at about 32-40° C. A rinse of THF (approximately 0.5 parts by weight) was used to complete the transfer. The reaction was held at about 35° C. for about 1 hour, then it was cooled. The reaction was quenched with water (approximately 3.7 parts by weight) while controlling the temperature at about 25-40° C. The reaction was further cooled and acidified with conc. hydrochloric acid (approximately 1.7× mole fraction) while controlling the temperature at about 10-20° C., to give a pH of about 3. The resulting suspension of product was stirred at about 0-5° C. for about 7 hours and then the product was collected by filtration and washed with a cold THF/water mixture. The product was dried in a vacuum dryer to yield approximately 1.7 parts by weight dry enol-lactone (about 0.6× mole fraction).

We claim:

1. A compound of Formula 1 or 2

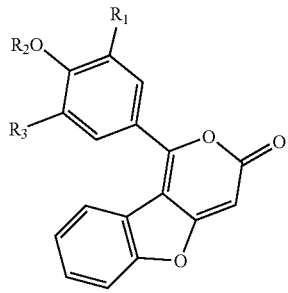
Formula 1

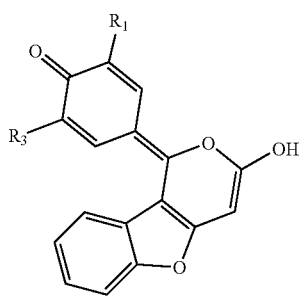
Formula 2 or a salt or tautomer thereof, wherein,
R$_1$ is independently H or halogen;
R$_2$ is H or —R$_{10}$—NR$_{11}$R$_{12}$, wherein
R$_{10}$ is C$_1$-C$_6$ alkyl;
R$_{11}$ and R$_{12}$ are independently H, C$_1$-C$_4$ alkyl; and;
R$_3$ is independently H or halogen.

2. A compound according to claim 1 wherein, R$_1$ and R$_3$ are, independently, a halogen, and R$_2$ is hydroxy (—OH).

3. A compound according to claim 1 wherein, R$_1$ and R$_3$ are iodo, and R$_2$ is hydroxy (—OH).

4. A method for making compounds according to Formulae 1-4

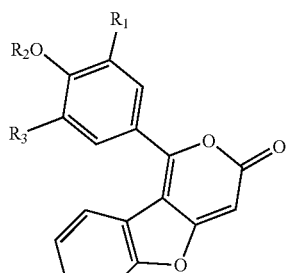
Formula 1

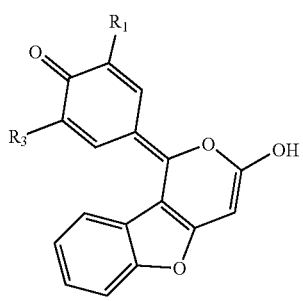
Formula 2

-continued

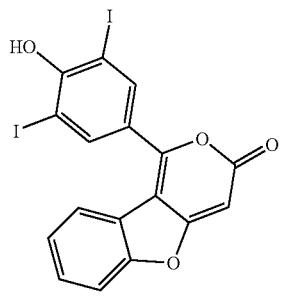

Formula 3

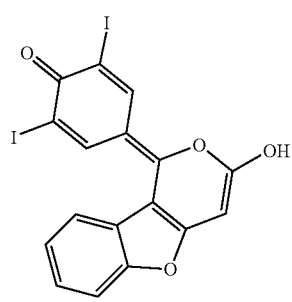

Formula 4 or a salt or tautomer thereof, wherein, $R_1$ is H or halogen;
$R_2$ is H or —$R_{10}$—$NR_{11}R_{12}$, wherein
  $R_{10}$ is $C_1$-$C_6$ alkyl;
  $R_{11}$ and $R_{12}$ are independently H, $C_1$-$C_4$ alkyl; and
$R_3$ is H or halogen;
comprising:
(a) reacting benzofuran-2-yl-acetic acid (BFAA) with a alkanol to make a BFAA ester;
(b) reacting the BFAA ester with p-anisoyl chloride (4-methoxybenzoyl chloride) to make a dialkyl aryl ketone;
(c) dealkylating the anisolic portion

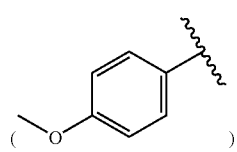

of the dialkyl aryl ketone to make a phenolic version

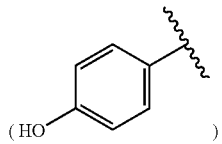

of the alkyl aryl ketone;
(d) converting the ester into its corresponding carboxylic acid;
(e) optionally halogenating; and
(f) converting the carboxylic acid-containing compound to an enol-lactone.

5. A method for making compounds according to Formula 5:

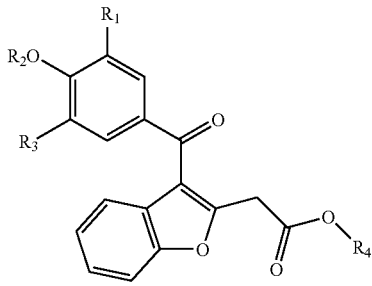

Formula 5 wherein,
$R_1$ is H or halogen;
$R_2$ is H or —$R_{10}$—$NR_{11}R_{12}$, wherein
  $R_{10}$ is $C_1$-$C_6$ alkyl;
  $R_{11}$ and $R_{12}$ are independently H, $C_1$-$C_4$ alkyl;
$R_3$ is H or halogen;
$R_4$ is $C_1$-$C_6$ alkyl; and
salts and tautomers thereof, comprising,
(a) reacting a compound according to claim 1 with ($C_1$-$C_6$) alkyl-containing alcohol to make an ester; and
(b) reacting the resulting compound with a halogenated amine according to X—$R_{10}$—$NR_{11}R_{12}$; wherein,
  X is a halogen;
  $R_{10}$ is $C_1$-$C_6$ alkyl; and
  $R_{11}$ and $R_{12}$ are independently H, $C_1$-$C_4$ alkyl to yield a compound of Formula 5.

6. The method according to claim 5 wherein the ($C_1$-$C_6$) alkyl-containing alcohol is (S)-2-butanol or (R)-2-butanol and the amine according to X—$R_{10}$—$NR_{11}R_{12}$ is 2-chloro-N,N-diethylethanamine hydrochloride or 2-chloro-N-ethyl-ethanamine hydrochloride.

* * * * *

UNITED STATES PATENT AND TRADEMARK OFFICE
CERTIFICATE OF CORRECTION

PATENT NO. : 7,498,449 B2
APPLICATION NO. : 11/457719
DATED : March 3, 2009
INVENTOR(S) : Pascal J. Druzgala et al.

It is certified that error appears in the above-identified patent and that said Letters Patent is hereby corrected as shown below:

At column 34, claim number 2, line number 37, please delete "$R_2$ is hydroxy (-OH)" and replace with --$R_2$ is H--

At column 34, claim number 3, line number 39, please delete "$R_2$ is hydroxy (-OH)" and replace with --$R_2$ is H--

Signed and Sealed this
Twelfth Day of February, 2013

Teresa Stanek Rea
*Acting Director of the United States Patent and Trademark Office*